(12) United States Patent
Zuo et al.

(10) Patent No.: US 10,330,665 B2
(45) Date of Patent: Jun. 25, 2019

(54) EVALUATING RESERVOIR OIL BIODEGRADATION

(71) Applicant: Schlumberger Technology Corporation, Sugar Land, TX (US)

(72) Inventors: Youxiang Zuo, Burnaby (CA); Oliver C. Mullins, Houston, TX (US); Richard Jackson, Cape Town (ZA); Ankit Agarwal, West Bengal (IN)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 555 days.

(21) Appl. No.: 14/933,807

(22) Filed: Nov. 5, 2015

(65) Prior Publication Data

US 2016/0123953 A1    May 5, 2016

(30) Foreign Application Priority Data

Nov. 5, 2014    (IN) ............................ 5574/CHE/2014

(51) Int. Cl.
*E21B 49/08*      (2006.01)
*G01N 33/28*     (2006.01)

(52) U.S. Cl.
CPC ......... *G01N 33/2888* (2013.01); *E21B 49/08* (2013.01)

(58) Field of Classification Search
CPC ............... G01N 33/2823; G01N 21/31; G01N 33/2888; E21B 2049/085; E21B 49/00; E21B 49/08

(Continued)

(56) References Cited

U.S. PATENT DOCUMENTS

| 4,994,671 A | 2/1991 | Safinya et al. |
| 5,331,156 A | 7/1994 | Hines et al. |

(Continued)

FOREIGN PATENT DOCUMENTS

WO    2012042397 A2    4/2012

OTHER PUBLICATIONS

Muskat, M. Distribution of non-reacting fluids in the gravitational field, Physical Review, vol. 35, Jun. 4, 1930, 1384-1393.

(Continued)

*Primary Examiner* — John E Breene
*Assistant Examiner* — Jeffrey P Aiello
(74) *Attorney, Agent, or Firm* — Michael Dae

(57) ABSTRACT

Upper and lower asphaltene weight fractions of fluid proximate ends of an oil column are obtained based on measured OD. Upper and lower maltene partial densities are obtained based on the asphaltene weight fractions. A maltene partial density distribution is obtained utilizing the maltene partial densities and a predetermined diffusion model. An asphaltene partial density distribution is obtained based on the maltene partial density distribution and an estimated mass density gradient. An asphaltene weight percentage is obtained based on the asphaltene partial density distribution and the mass density gradient. The asphaltene weight percentage distribution is converted to an OD distribution utilizing a predetermined correlation. An optimization then reduces differences between the OD distribution and the measured OD data to within a predetermined range to refine a biodegradation time of the predetermined diffusion model. A viscosity distribution may be obtained based on the optimized OD distribution.

20 Claims, 10 Drawing Sheets

(58) Field of Classification Search
USPC .............. 166/250.01; 324/303, 324; 702/11; 703/2, 9
See application file for complete search history.

(56) References Cited

U.S. PATENT DOCUMENTS

| | | | |
|---|---|---|---|
| 6,476,384 B1 | 11/2002 | Mullins et al. | |
| 7,526,953 B2 | 5/2009 | Goodwin et al. | |
| 7,822,554 B2 | 10/2010 | Zuo et al. | |
| 7,920,970 B2 | 4/2011 | Zuo et al. | |
| 7,996,154 B2* | 8/2011 | Zuo | E21B 47/102 175/40 |
| 8,271,248 B2 | 9/2012 | Pomerantz et al. | |
| 8,332,194 B2* | 12/2012 | Morales | E21B 43/34 703/10 |
| 8,434,356 B2 | 5/2013 | Hsu et al. | |
| 8,805,617 B2 | 8/2014 | Zuo et al. | |
| 8,996,346 B2* | 3/2015 | Zuo | E21B 47/10 703/10 |
| 9,410,936 B2* | 8/2016 | Zuo | E21B 49/00 |
| 2005/0246151 A1* | 11/2005 | DiFoggio | G01V 1/50 703/10 |
| 2009/0248310 A1* | 10/2009 | Zuo | E21B 47/102 702/11 |
| 2009/0312997 A1 | 12/2009 | Freed et al. | |
| 2012/0232799 A1 | 9/2012 | Zuo et al. | |
| 2012/0232859 A1 | 9/2012 | Pomerantz et al. | |
| 2012/0296617 A1 | 11/2012 | Zuo et al. | |
| 2013/0112406 A1 | 5/2013 | Zuo et al. | |
| 2014/0200810 A1 | 7/2014 | Zuo et al. | |
| 2014/0360257 A1* | 12/2014 | Indo | E21B 47/102 73/152.28 |
| 2014/0360259 A1* | 12/2014 | Indo | E21B 49/088 73/152.55 |
| 2015/0176407 A1* | 6/2015 | Indo | G01N 21/31 702/6 |
| 2015/0185360 A1 | 7/2015 | Freed et al. | |
| 2015/0205000 A1* | 7/2015 | Perkins | G01N 21/31 702/8 |
| 2016/0146004 A1 | 5/2016 | Wang et al. | |

OTHER PUBLICATIONS

Onsager, L. Reciprocal relations in irreversible processes: I, Phys. Rev. 37, Feb. 15, 1931, 405-426.
Onsager, L. Reciprocal relations in irreversible processes: II, Phys. Rev. 38 (Dec. 15, 1931), 2265-2279.
Ghorayeb, K. and Firoozabadi, A. Modeling multicomponent diffusion and convection in porous media, SPE Journal 5.02 (Jun. 2000): 158-171.
Hoier, L., and Whitson, C. H. 2000. Compositional grading, theory and practice. SPE Paper 63085. 2000 SPE Annual Technical Conference and Exhibition, Dallas, Texas, Oct. 1-4, 2000, (16 pages).
Alboudwarej, H., Akbarzadeh, K., Beck, J., Svrcek, W. Y. and Yarranton, H. W. (2003), Regular solution model for asphaltene precipitation from bitumens and solvents. AIChE J., 49: 2948-2956.
Mullins, O. C. The Modified Yen Model. Energy Fuels, Jan. 19, 2010, 24(4), 2179-2207.
Zuo, J. Y., Freed, D., Mullins, O. C., Zhang, D., & Gisolf, A. (Jan. 2010). Interpretation of DFA Color Gradients in Oil Columns Using the Flory-Huggins Solubility Model, SPE 130305, Beijing, China, Jul. 8-10, 2010.
Zuo, J. Y., Zhang, D., Dubost, F. X., Dong, C., Mullins, O., O'Keefe, M., & Betancourt, S. (2011). Equation-of-State-Based Downhole Fluid Characterization. SPE Journal, 16(01), 115-124.
Mullins, O. C., et al., (2012) Advances in asphaltene science and the Yen-Mullins model. Energy & Fuels, 26(7), 3986-4003.
Zuo, J. Y., Mullins, O. C., Freed, D., Elshahawi, H., Dong, C., & Seifert, D. J. (2013). Advances in the Flory-Huggins-Zuo equation of state for asphaltene gradients and formation evaluation. Energy & Fuels, 27(4), 1722-1735.
Zuo, J. Y., Mullins, O. C., Mishra, V., Garcia, G., Dong, C., & Zhang, D. (2012). Asphaltene grading and tar mats in oil reservoirs. Energy & Fuels, 26(3), 1670-1680.
Mullins, O. C., Seifert, D. J., Zuo, J. Y., & Zeybek, M. (2012). Clusters of asphaltene nanoaggregates observed in oilfield reservoirs. Energy & Fuels, 27(4), 1752-1761.
Mullins, O.C., Zuo, J.Y., Wang, K., Hammond, P.S., Santo, I.D., Dumont, H., Mishra, V. K., Chen, L., Pomerantz, A.E., Jong, C., Elshahawi, H., Seifert, D.J., The Dynamics of Reservoir Fluids and their Substantial Systematic Variations, Petrophysics, vol. 55, No. 2, Apr. 2014, pp. 96-112.
Freed, D.E., Mullins, O.C., Zuo, J.Y., Heuristics for Equilibrium Distributions of Asphaltenes in the Presence of GOR Gradients, Energy & Fuels, accepted for publication, 2014, pp. 4859-4869.

* cited by examiner

EVALUATING RESERVOIR OIL BIODEGRADATION

CROSS-REFERENCE TO RELATED APPLICATIONS

This application claims priority to India Patent Application Number 5574/CHE/2014, filed Nov. 5, 2014, which is herein incorporated by reference.

BACKGROUND OF THE DISCLOSURE

Biodegradation of oil in subterranean reservoirs may create substantial compositional gradients, and/or render composition distributions in a reservoir far away from equilibration, thus yielding substantial viscosity variations. Such behavior is conventionally modeled utilizing very complex models.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method in which a downhole tool is conveyed within a wellbore. The wellbore extends from a wellsite surface into a subterranean oil column. The downhole tool is in communication with surface equipment located at the wellsite surface. The method includes operating the downhole tool and/or the surface equipment to measure optical density (OD) of fluid at multiple depths within the oil column, obtain upper and lower asphaltene weight fractions of fluid proximate respective ends of the oil column based on the measured OD, and obtain upper and lower maltene partial densities of the fluid proximate the respective oil column ends based on the respective upper and lower asphaltene weight fractions. A maltene partial density distribution along depth within the oil column is then obtained utilizing the upper and lower maltene partial densities and a predetermined diffusion model. An asphaltene partial density distribution along depth within the oil column is then obtained based on the maltene partial density distribution and a mass density gradient estimated with respect to depth within the oil column. An asphaltene weight percentage distribution along depth within the oil column is then obtained based on the asphaltene partial density distribution and the mass density gradient. The asphaltene weight percentage distribution is then converted to an OD distribution utilizing a predetermined correlation between asphaltene weight fraction and OD. An optimization process is then performed to reduce differences between the OD distribution and the measured OD data to within a predetermined range and refine a biodegradation time of the predetermined diffusion model.

The present disclosure also introduces a system that includes a downhole tool conveyable within a wellbore that extends from a wellsite surface into a subterranean oil column, and surface equipment located at the wellsite surface and in communication with the downhole tool. The downhole tool and the surface equipment are collectively operable to measure OD of fluid at multiple depths within the oil column, obtain upper and lower asphaltene weight fractions of fluid proximate respective ends of the oil column based on the measured OD, and obtain upper and lower maltene partial densities of the fluid proximate the respective oil column ends based on the respective upper and lower asphaltene weight fractions. The downhole tool and the surface equipment are also collectively operable to obtain a maltene partial density distribution along depth within the oil column utilizing the upper and lower maltene partial densities and a predetermined diffusion model, obtain an asphaltene partial density distribution along depth within the oil column based on the maltene partial density distribution and a mass density gradient estimated with respect to depth within the oil column, and obtain an asphaltene weight percentage distribution along depth within the oil column based on the asphaltene partial density distribution and the mass density gradient. The downhole tool and the surface equipment are also collectively operable to convert the asphaltene weight percentage distribution to an OD distribution utilizing a predetermined correlation between asphaltene weight fraction and OD, and perform an optimization process to reduce differences between the OD distribution and the measured OD data to within a predetermined range and refine a biodegradation time of the predetermined diffusion model.

The present disclosure also introduces a computer program product that includes a non-transitory, computer-readable medium and instructions recorded on the medium for operating a downhole tool positioned within a wellbore and surface equipment in communication with the downhole tool. The instructions are to measure OD of fluid at multiple depths within the oil column, obtain upper and lower asphaltene weight fractions of fluid proximate respective ends of the oil column based on the measured OD, and obtain upper and lower maltene partial densities of the fluid proximate the respective oil column ends based on the respective upper and lower asphaltene weight fractions. The instructions are also to obtain a maltene partial density distribution along depth within the oil column utilizing the upper and lower maltene partial densities and a predetermined diffusion model, obtain an asphaltene partial density distribution along depth within the oil column based on the maltene partial density distribution and a mass density gradient estimated with respect to depth within the oil column, and obtain an asphaltene weight percentage distribution along depth within the oil column based on the asphaltene partial density distribution and the mass density gradient. The instructions are also to convert the asphaltene weight percentage distribution to an OD distribution utilizing a predetermined correlation between asphaltene weight fraction and OD, and perform an optimization process to reduce differences between the OD distribution and the measured OD data to within a predetermined range and refine a biodegradation time of the predetermined diffusion model.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
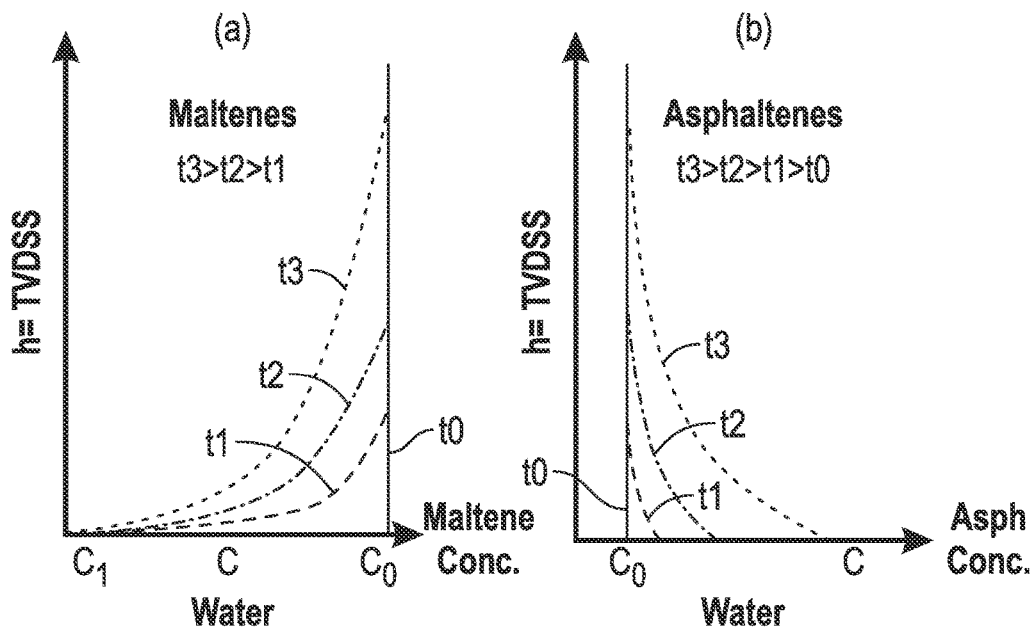
FIG. 1 is a graph depicting one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity, and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Biodegradation of oil columns occurs at the oil-water contact, because the microbes live in the water and consume oil chemical components. The microbes consume specific chemical species in the crude oils. For example, n-alkanes are the first chemical species consumed by microbes in the biodegradation process as indicated in the Peters-Moldowan rank of biodegradation.

Large fluid gradients have been observed in cases of biodegradation. Diffusion has been shown to be a rate-controlling component of biodegradation. The present disclosure introduces one or more aspects of thermodynamically modeling the effect of biodegradation on asphaltene and viscosity gradients.

Diffusion of alkanes to the oil-water contact is presumed to be the rate-limiting step in this process. The predominant effect on asphaltene concentration is consistent with consumption of alkanes and some alkylaromatics. The thermodynamic model may account for both the upper oil column, which is in thermodynamic equilibrium, and the lower section of the oil column, which is dominated by the dynamic processes of diffusion and biodegradation. The thermodynamic model of asphaltene gradients, even in situations where the reservoir is undergoing dynamic processes, may be utilized within the scope of the present disclosure to, for example, advance reservoir engineering modeling and, perhaps, increase oil production efficiency.

An equation of state (EoS) is set forth below in Equation (1).

$$\frac{OD(h_2)}{OD(h_1)} = \frac{\phi_a(h_2)}{\phi_a(h_1)} = \exp\left\{\frac{v_a g(\rho - \rho_a)(h_2 - h_1)}{RT} + \frac{v_a}{RT}\left[(\delta_a - \delta)^2_{h_1} - (\delta_a - \delta)^2_{h_2}\right] + \left[\left(\frac{v_a}{v}\right)_{h_2} - \left(\frac{v_a}{v}\right)_{h_1}\right]\right\} \quad (1)$$

where OD, R, $\phi$, v, $\delta$, T, g, $\rho$, and h are the optical density, universal gas constant, volume fraction, molar volume, solubility parameter, temperature, gravitational acceleration, density, and depth, respectively. The subscript a denotes the properties of asphaltenes, and the subscripts $h_1$ and $h_2$ correspond to the properties at depths $h_1$ and $h_2$, respectively. The solubility parameter, molar volume, and density of bulk fluids, temperature, pressure, and compositions are dependent on depth.

The EoS of Equation (1) may be utilized to account for asphaltene gradients in oilfield reservoirs and in laboratory centrifugation experiments. It relies on the colloidal characterization of the crude oils. For example, for heavy oils, large asphaltene gradients are obtained due to the relatively large cluster size.

For low-GOR (gas/oil ratio) fluids, the solubility and entropy terms may approximately be canceled out due to the opposite influence on the asphaltene concentration gradient. Thus, Equation (1) may be rewritten as set forth below in Equation (2).

$$\frac{OD(h_2)}{OD(h_1)} = \frac{\phi_a(h_2)}{\phi_a(h_1)} = \exp\left\{\frac{v_a g(\rho - \rho_a)(h_2 - h_1)}{RT}\right\} \quad (2)$$

However, the FHZ EoS is most effectively employed to estimate the asphaltene gradient due to low-GOR oil. That is, the solubility term of the FHZ EoS is largely invariant for a relatively homogenous low-GOR crude oil at low reservoir pressure. Accordingly, while the FHZ EoS may be sufficiently accurate near the top of the oil column, OD measurements near the oil-water contact (OWC) at the base of the oil column are substantially higher than predicted by the FHZ EoS. Thus, thermodynamic equilibrium of asphaltenes applies over the upper portion (e.g., upper half) of the oil column, while a substantial disequilibrium in asphaltene concentration applies in the lower portion (e.g., lower half) of the oil column.

Such disequilibrium is related to the fact that, under certain conditions, bacteria, yeasts, molds, filamentous fungi, and/or other living microorganisms can alter and/or metabolize various classes of compounds present in oil. Such processes may collectively be referred to as oil biodegradation.

Crude oils in reservoirs with a temperature less than 80 degrees C. may be biodegraded. Biodegradation increases the asphaltene content and decreases the gasoline and diesel fractions of the reservoir crude oil, thereby decreasing the value of the crude oil. Moreover, biodegradation occurs at the oil-water contact, and thus produces large fluid gradients in the oil column. Consequently, the present disclosure introduces one or more aspects pertaining to identifying when biodegradation has occurred and the corresponding distributions of crude oil properties in the reservoir.

Gas chromatograph (GC) and/or mass spectroscopy (MS) have been utilized for oil biodegradation investigation of samples of dead oil, which is oil at sufficiently low pressure that it contains no dissolved gas or a relatively thick oil or residue that has lost its volatile components. In contrast, the present disclosure introduces oil biodegradation investigation utilizing DFA of downhole samples (e.g., live oil).

A schematic diagram for an example biodegradation process is shown in FIG. 1. A one-dimension model is taken into account. At the OWC, the depth h=0, and increases upwards. In FIG. 1 (and others), the depth h is TVDSS (or TVDss), which represents true vertical depth (TVD) minus the elevation above mean sea level of the depth reference point of the well. The depth reference point may be the drill floor or the kelly bushing, for example. The TVD is the absolute vertical distance between the depth reference point and the point in the wellbore and/or subterranean formation (in contrast to the measured depth (MD) along the path of a wellbore).

Figure 2:
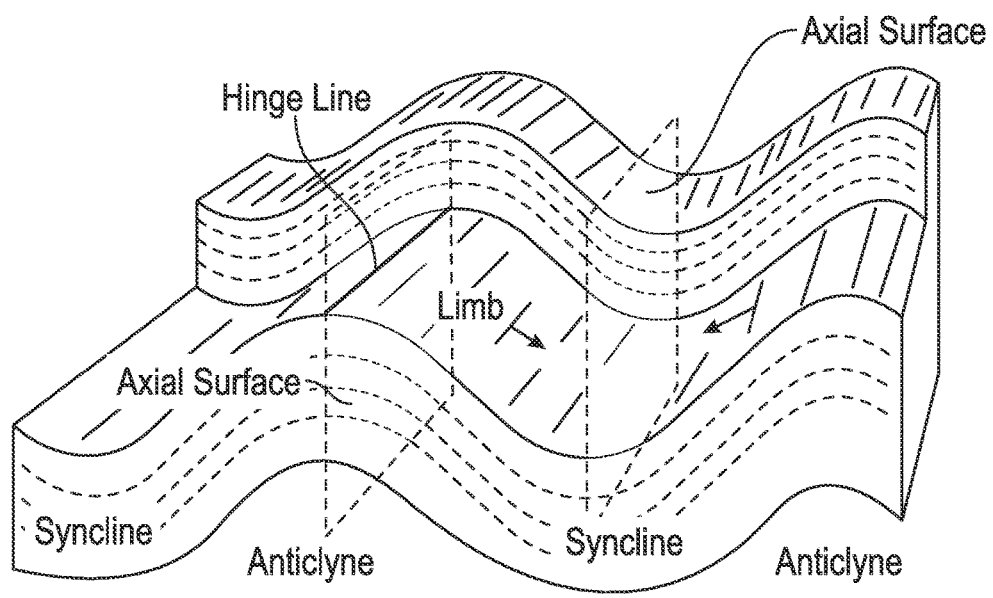
FIG. 2 is a schematic diagram depicting one or more aspects of the present disclosure.

For anticline reservoirs, the dip angle may be utilized to convert real distance to vertical distance. Anticline refers to an arch-shaped fold in rock in which rock layers are upwardly convex. The oldest rock layers form the core of the fold, and progressively younger rocks occur outward from the core. Anticlines form hydrocarbon traps, particularly in folds with reservoir-quality rocks in their core and impermeable seals in the outer layers of the fold. A syncline is the opposite type of fold, having downwardly convex layers with young rocks in the core. FIG. 2 is a schematic diagram of parts of example anticlines and synclines.

The biodegradation process may be modeled according to one or more aspects of the present disclosure. Such model may be developed as follows:

1. Utilize a one-dimensional model.
2. Assume biodegradation occurs solely at the OWC.
3. Living microorganisms consume the alkanes rapidly in comparison with diffusion times of the components to the OWC. Thus, presume the rate-limiting step to be alkane diffusion down to the OWC.
4. Divide whole oil components into two groups: maltenes (m) and asphaltenes (a).
5. Assume the initial compositions of the reservoir are at equilibrium.
6. Assume the alkane concentration does not change (e.g., from an initial value) at locations far away from the OWC.
7. Ignore diffusion of asphaltenes up the oil column because biodegradation makes solvents (maltenes) better for dissolving asphaltenes, which may compensate for upward diffusion of asphaltenes.

Figure 3:
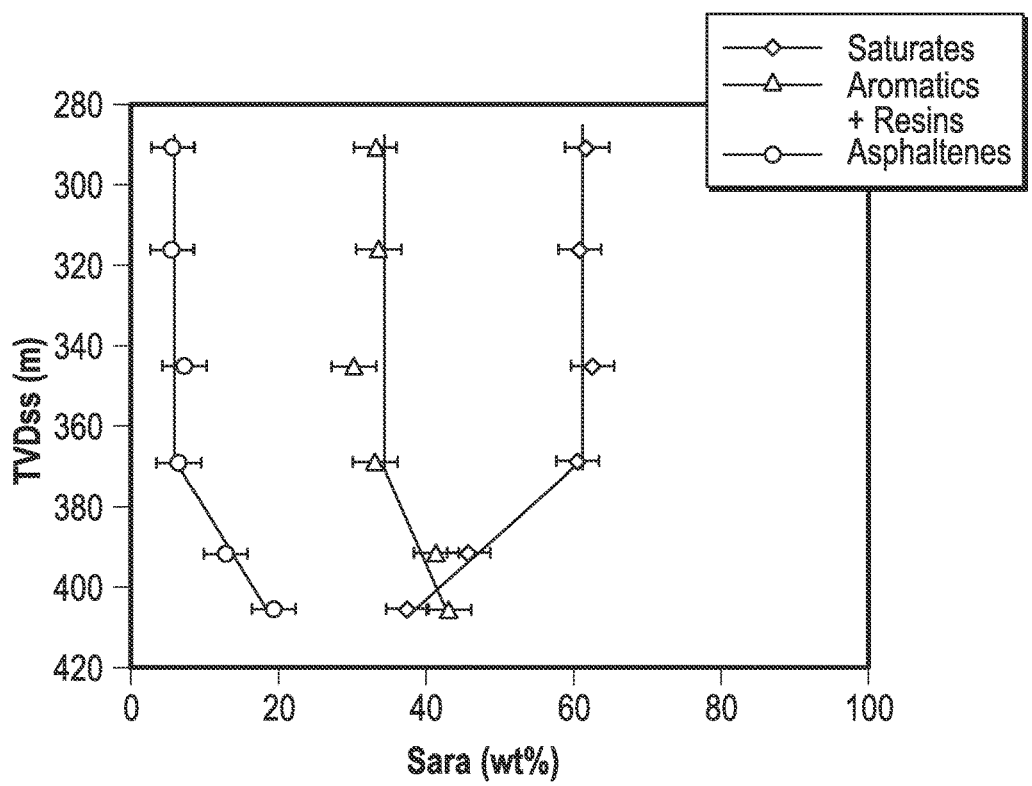
FIG. 3 is a graph depicting one or more aspects of the present disclosure.

In the example depicted in FIG. 3 (in which the depth direction is opposite to that shown in FIG. 1), there are no compositional gradients in the shallow layers between about 290 m and about 370 m. However, large gradients are observed for saturates and asphaltenes. The gradient of the summation of aromatics and resins is slight, at least slight enough that it does not substantially change.

The diffusion in FIG. 1 is governed by Fick's second law, as set forth below in Equation (3).

$$\frac{\partial \bar{\rho}_m}{\partial t} = D \frac{\partial^2 \bar{\rho}_m}{\partial h^2} \tag{3}$$

where $\bar{\rho}_m$ is the mass concentration (partial density) of the maltenes which contain alkanes that can be consumed by microbes. D, t, and h are the effective diffusion coefficients of the maltenes (actually alkanes) independent of concentration, time, and depth, respectively.

Initial conditions of a reservoir just prior to biodegradation at all depths (h) may be given by Equation (4), set forth below.

$$\bar{\rho}_m = \bar{\rho}_{m0} \text{ at } t=0 \tag{4}$$

where $\bar{\rho}_{m0}$ is the initial mass concentration (partial density) of the maltenes.

Because biodegradation occurs at the OWC where microbes live and consume the alkanes (such that alkane concentration is substantially zero), the concentration of maltenes at the OWC can be considered approximately as a constant although the loss of alkane components decreases the oil volume yielding an increase in asphaltene concentration. Then, $\bar{\rho}_{m1}$ (the partial density of maltenes at the base of the oil column) can be treated as an adjustable parameter if no data is available. The first boundary condition may then be expressed as set forth below in Equation (5).

$$\bar{\rho}_m = \bar{\rho}_{m1} \text{ for } h=0 \text{ at } t>0 \tag{5}$$

Because the concentration of maltenes remains unchanged at shallow depth far away from the OWC due to lack of biodegradation or fresh oil charges into the top of the reservoir, the second boundary conditions may be expressed as set forth below in Equation (6).

$$\bar{\rho}_m = \begin{cases} \bar{\rho}_m & \text{at } h < \infty \\ \bar{\rho}_{m0} & \text{at } h = \infty \end{cases} \tag{6}$$

Consequently, according to the initial and boundary conditions, the analytical solution to Equation (3) may be expressed as set forth below in Equation (7).

$$\frac{\bar{\rho}_m - \bar{\rho}_{m1}}{\bar{\rho}_{m0} - \bar{\rho}_{m1}} = \text{erf}\left(\frac{h}{2\sin(\alpha)\sqrt{Dt}}\right) \quad \bar{\rho}_{m0} > \bar{\rho}_{m1} \tag{7}$$

where erf is the error function and $\alpha$ is the dip angle.

As described above, the oil components may be divided into two groups: alkanes and other maltenes (m) and asphaltene (a). Consequently, the fluid density ($\rho$) at each depth, which can be measured by a DV-rod density/viscosity sensor and/or other sensors, may be expressed in terms of the partial density of maltenes ($\bar{\rho}_m$) and the partial density of asphaltenes ($\bar{\rho}_a$), as set forth below in Equation (8).

$$\bar{\rho}_a = \rho - \bar{\rho}_m \qquad (8)$$

It is also known that the weight (mass) fraction may be calculated as set forth below in Equation (9).

$$w_i = \frac{\bar{\rho}_i}{\rho} \qquad (9)$$

As mentioned above, fluid density may be measured downhole using a DV-rod sensor and/or one or more other types of density sensors. Accordingly, three parameters remain undetermined: $\bar{\rho}_{m0}$, $\bar{\rho}_{m1}$, and t.

The fluid density changes with depth are substantially caused by the reduction of alkanes and the increase in asphaltenes toward the OWC. Thus, if gas chromatography and SARA (saturate, asphaltene, resins, and aromatics) analysis data are available, then $\bar{\rho}_{m0}$ and $\bar{\rho}_{m1}$ may be estimated, such that t may be obtained by fitting the measured asphaltene gradient data of the lower portion (e.g., half) of the oil column.

Thus, to reiterate one or more of the aspects described above, the initial fluid of the oil column may be assumed to be equilibrated. At the beginning of the biodegradation, microbes consume alkanes at the OWC, thus yielding an alkane (maltene) concentration contrast. The alkane concentration contrast causes the alkanes to diffuse downward. The microbes then consume the alkanes that diffused down at or near the OWC. Because biodegradation processes are more rapid than diffusion, the limiting factor is alkane diffusion. This process continues slowly. The alkanes gradually disappear upward, and the concentration of maltenes decreases upward to shallower depths with time. Reservoir fluid density and fluid density gradients with depth can be measured at reservoir conditions by DFA and/or determined by measurements from fluid samples in the PVT laboratory. The oil density may then be populated based on these measurements. With the density gradient distribution, the mass concentration of asphaltenes may be determined, and then the mass fraction of asphaltenes. Thus, the asphaltene mass percentage with depth and time may be obtained. Then, time may be adjusted to match the DFA measured OD data. Asphaltene weight fraction may be converted to OD using, for example, a correlation developed from analysis of the phase behavior from laboratory measurements and experimental data.

Oil viscosity plays a central role in well productivity and displacement efficiency, and impacts completion strategies and field development plans. Accurately assessing areal and vertical variations of viscosity may lead to more realistic reservoir simulation and field development models. It has been demonstrated that oil viscosity varies exponentially with OD, such that viscosity can be related to OD by the diffusive model introduced above.

An example implementation of the workflow introduced above may be described as follows:

1. Utilize the FHZ EoS to match the OD data measured by DFA.
2. If the FHZ EoS does not provide adequate matching for a substantial lower portion of the oil column (e.g., the lower half), assess whether biodegradation may be present (e.g., by determining if the reservoir is shallow and the temperature is less than about 80 degrees C.).
3. Populate the density gradient by fitting the data of measured density vs. depth.
4. For the top of the oil column, utilize the FHZ EoS to obtain the equilibrium asphaltene gradient, then obtain asphaltene weight fraction ($w_{a0}$), then measure fluid mass density ($\rho_0$) utilizing downhole sensors. Utilize this information to obtain $\bar{\rho}_{m0}$ (which is known due to $\bar{\rho}_{m0} = (1 - w_{a0})\rho_0$).
5. Similarly, for the base of the oil column, measure mass density and mass fraction of maltenes, then obtain $\bar{\rho}_{m1}$.
6. Assume the biodegradation time (t).
7. Determine the maltene partial density ($\bar{\rho}_m$) distribution with respect to depth at the assumed time (e.g., utilizing Equation (7) set forth above).
8. Determine the asphaltene partial density (e.g., utilizing Equation (8) set forth above, because $\bar{\rho}_m$ and $\rho$ are known).
9. Determine the asphaltene weight fraction (e.g., utilizing Equation (9) set forth above).
10. Convert the asphaltene weight fraction to OD (e.g., utilizing a linear correlation between asphaltene content and OD).
11. Compare the asphaltene weight fraction converted OD with the DFA-measured OD and assess whether best matching exists.
12. If best matching doesn't yet exist, then update t and repeat elements 7-11. Otherwise, assume best fitting exists.
13. Relate viscosity to OD (e.g., utilizing an exponential function fit).
14. Output results.

Figure 4:
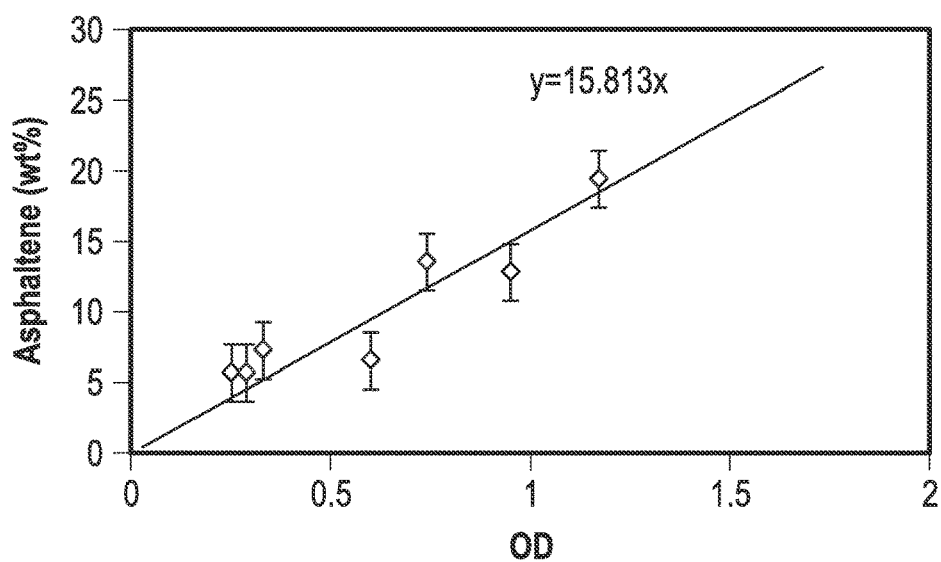
FIG. 4 is a graph depicting one or more aspects of the present disclosure.

To provide an example implementing the workflow described above, consider a shallow reservoir that is undergoing biodegradation. The reservoir temperature is about 57 degrees C. The asphaltene weight percentage (wt %) relative to optical density is depicted in FIG. 4. As depicted therein, a linear relation is obtained.

Figure 5:
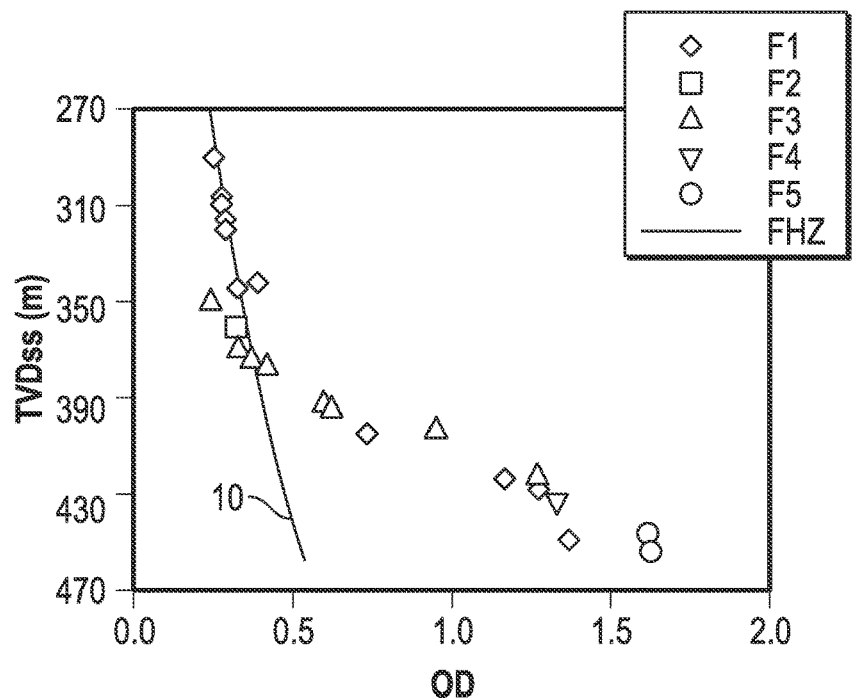
FIG. 5 is a graph depicting one or more aspects of the present disclosure.

Note that this is for low-GOR oil. Thus, utilization of the FHZ EoS with a gravity term is applicable to estimating the equilibrium asphaltene gradient. The result is depicted in FIG. 5, a comparison of DFA-measured OD to the FHZ EoS predictions. For example, FIG. 5 depicts example OD measurements obtained at various depths in multiple wells in a field, including data from multiple subterranean formations, beds, layers, reservoirs, and/or other features denoted in FIG. 5 as F1, F2, F3, F4, and F5. FIG. 5 also depicts a corresponding FHZ EoS prediction (reference numeral 10) for the field. It can be seen in FIG. 5 that the deeper layers have substantially greater OD (and thus asphaltene wt %) relative to the equilibrium distribution predicted by the FHZ EoS.

Figure 6:
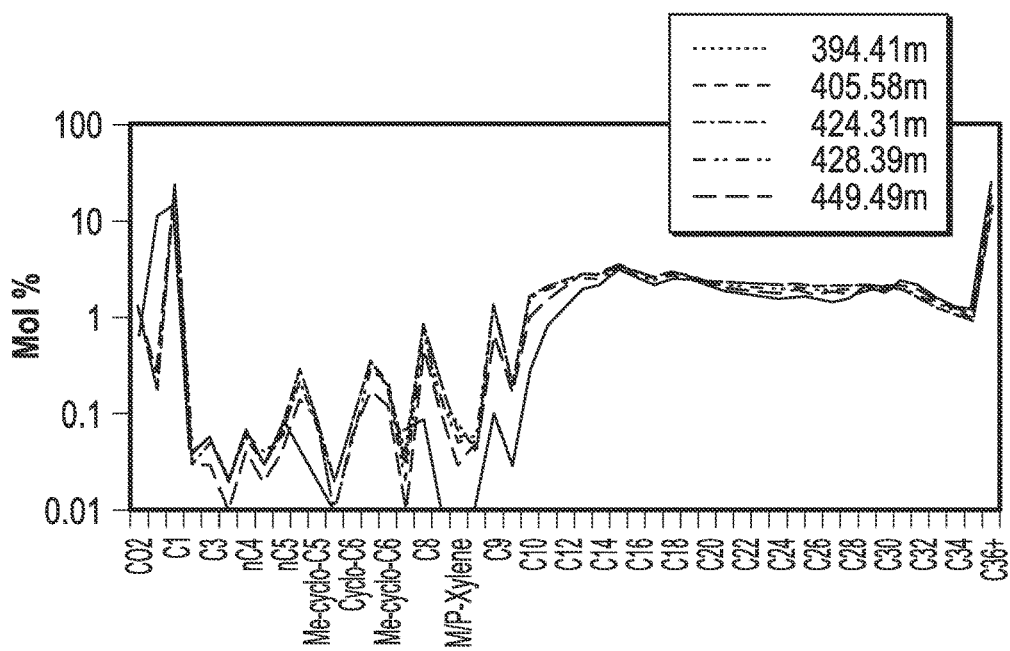
FIG. 6 is a graph depicting one or more aspects of the present disclosure.
Figure 7:
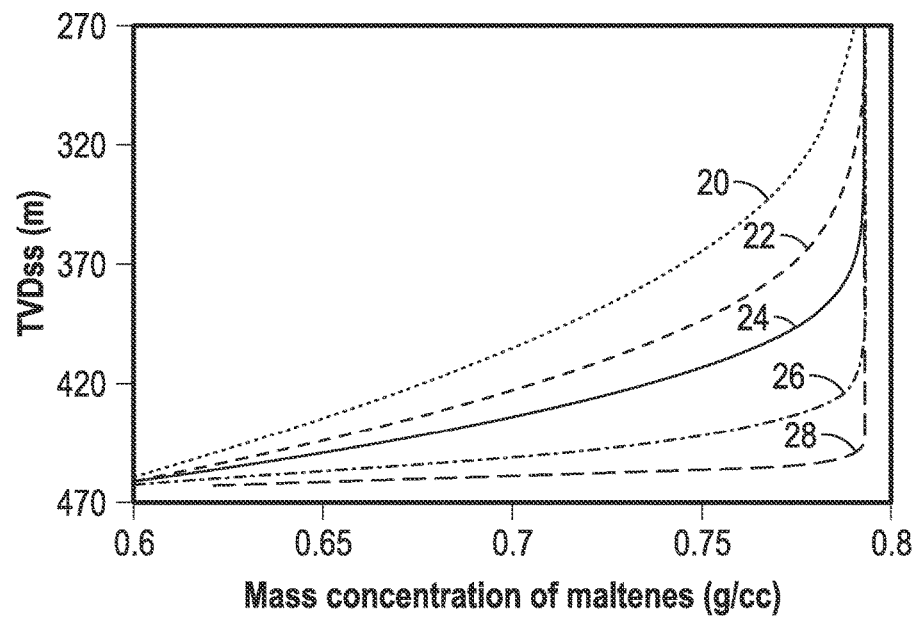
FIG. 7 is a graph depicting one or more aspects of the present disclosure.

Example OBM corrected GC compositions from different depths are depicted in FIG. 6. Among other aspects depicted in FIG. 6, it can be seen that alkanes (C2-C9) exist in very low or negligible concentrations relative to other components. The diffusion model introduced in this disclosure is used in this case. It is assumed that the alkane diffusion coefficient $D = 5.0 \times 10^{-7}$ cm$^2$/s and the dip angle is 15 degrees. Thus, Equation (8) set forth above may be utilized to calculate the alkane distribution with respect to time and depth. An example result for a field is depicted in FIG. 7, in which mass concentrations of maltenes relative to depth are plotted for timespans of thirty million years (reference numeral 20), fifteen million years (reference numeral 22), 7.5 million years (reference numeral 24), 1.5 million years (reference numeral 26), and 0.15 million years (reference numeral 28).

For example, just before the start of biodegradation, it is assumed that fluids of the oil column are substantially homogeneous. At the start of biodegradation, microorganisms consume alkanes at the OWC, yielding alkane concentration contrast. Such alkane concentration contrast makes alkanes diffuse downward relative to the OWC. Microorganisms then consume the alkanes diffused down at the OWC. This process continues, and alkanes gradually disappear upward to shallow layers.

Figure 8:
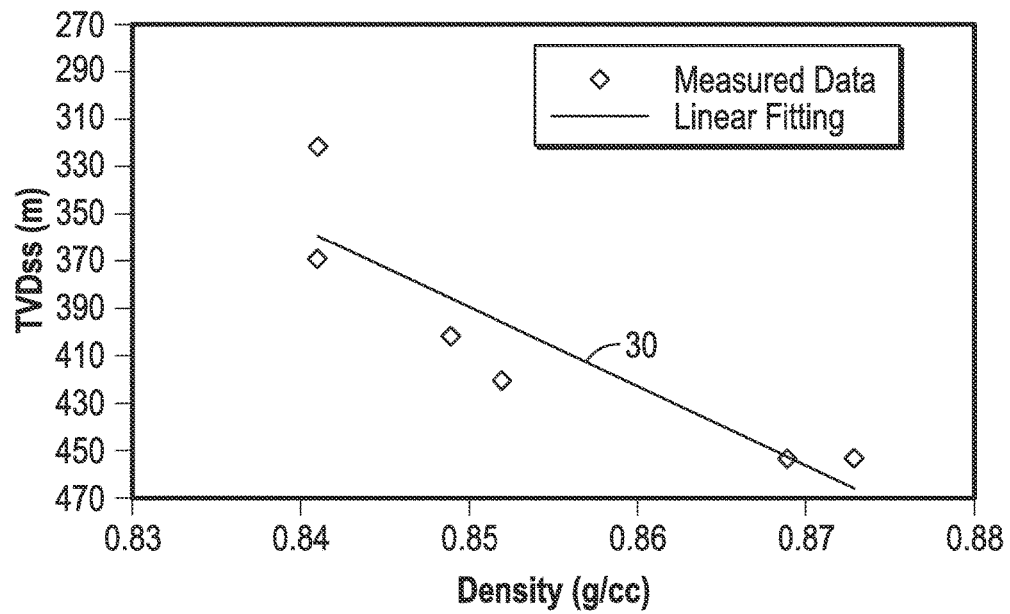
FIG. 8 is a graph depicting one or more aspects of the present disclosure.

Example density changes with respect to depth are depicted in FIG. 8. In FIG. 8, the data points are from different logging runs in multiple wells in a field, and the line (reference numeral 30) is a linear fitting of the data points. The example shown in FIG. 8 depicts a linear fitting of the data points as y=3309.2 x−2423.3.

Figure 9:
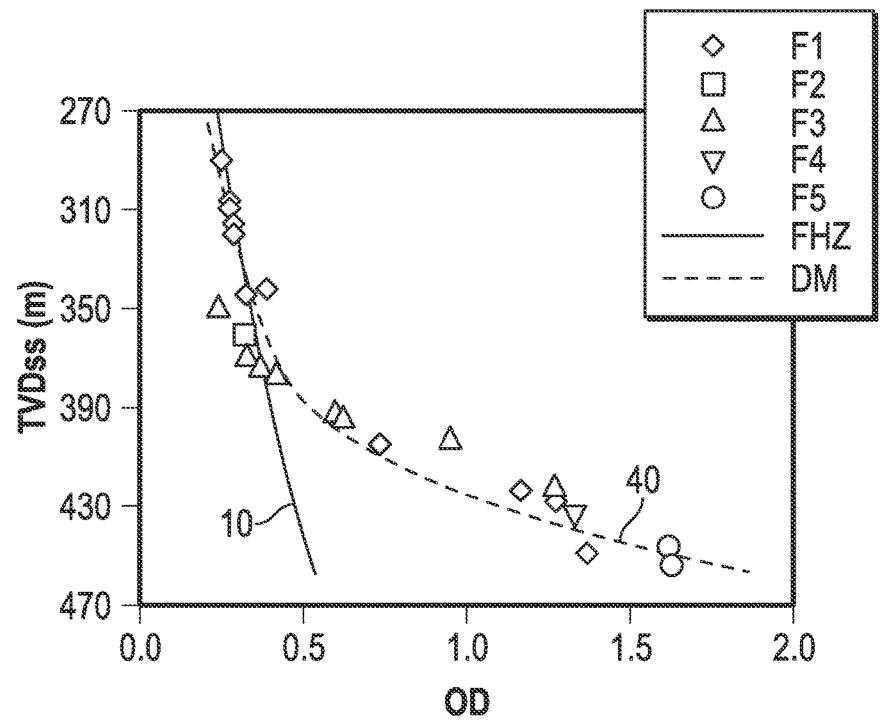
FIG. 9 is a graph depicting one or more aspects of the present disclosure.

The asphaltene weight fraction may be converted to OD using the correlation depicted in FIG. 4. Thus, the optimized t=7 0.5×10$^6$ years if D=5×10$^{-7}$ cm$^2$/s and α=15 degrees. Example results are depicted in FIG. 9. For example, FIG. 9 depicts OD measurements obtained at various depths in multiple wells depicted in FIG. 5 (including data from subterranean features F1, F2, F3, F4, and F5), as well as the FHZ EoS prediction (reference numeral 10) for the field and the corresponding diffusion model results (reference numeral 40) according to aspects of the present disclosure. It can be seen in FIG. 9 that the FHZ EoS (10) gives the equilibrium distribution of OD, whereas the diffusion model (40) substantially matches the OD gradient.

Moreover, viscosity varies exponentially with OD. Thus, viscosity may be related to the OD calculated by the model, as set forth below in Equation (10).

$$\mu=11.087\exp(1.4208OD) \quad (10)$$

Figure 10:
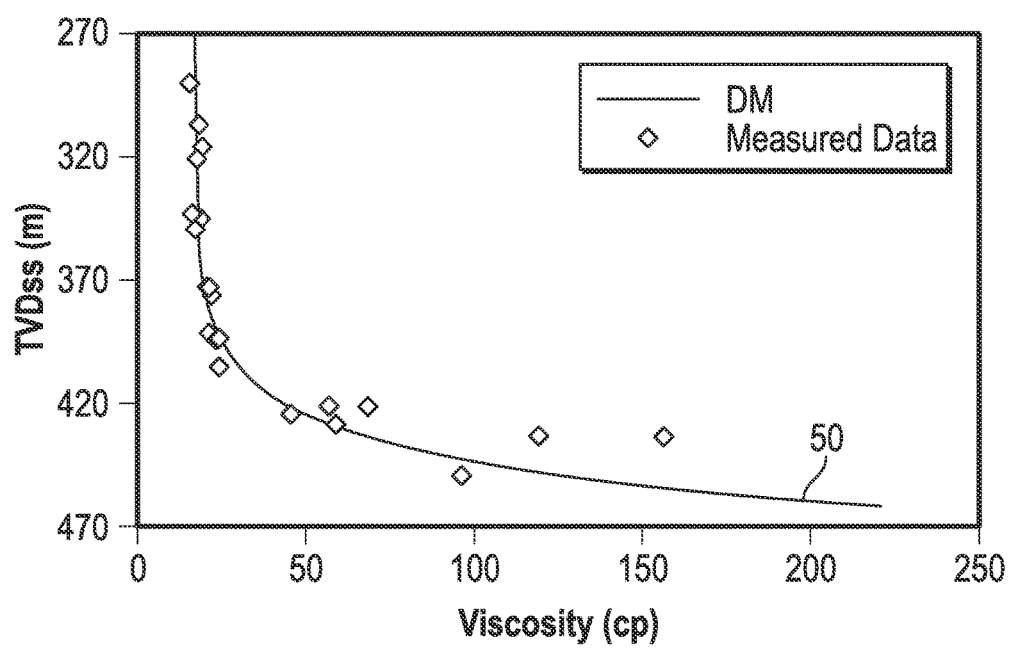
FIG. 10 is a graph depicting one or more aspects of the present disclosure.

Example results are depicted in FIG. 10, illustrating the viscosity gradient predicted by the viscosity model. In FIG. 10, the data points are from different logging runs in multiple wells in a field, and the line (reference numeral 50) depicts the results achieved utilizing the diffusion model for the field.

Figure 11:
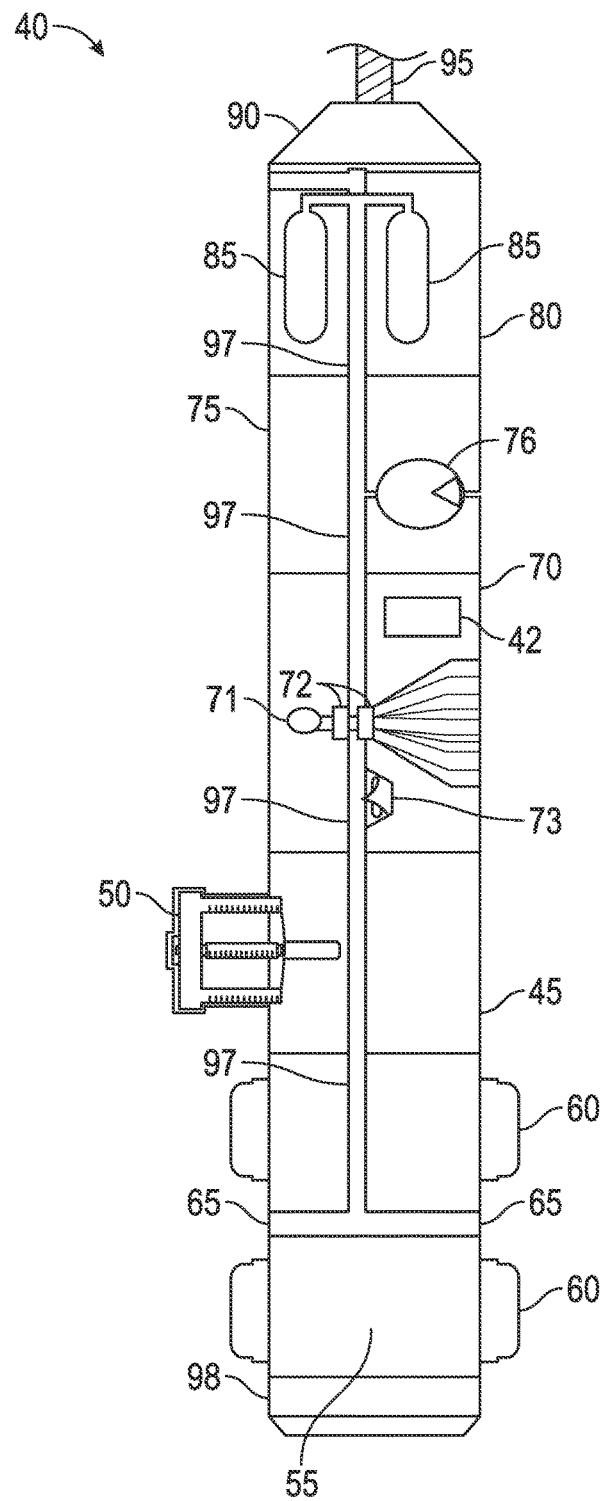
FIG. 11 is a schematic view of at least a portion of an example implementation of apparatus according to one or more aspects of the present disclosure.

FIG. 11 is a schematic view of at least a portion of an example implementation of a formation tester and/or other downhole tool or tool string apparatus 40 according to one or more aspects of the present disclosure. The apparatus 40 may be utilized to obtain the DFA measurements described above, such as spectrometry data, OD data, pressure data, temperature data, density data, viscosity data, and/or others.

The apparatus 40 comprises a probe module 45 comprising one or more probes 50. The apparatus 40 may also or instead comprise a packer module 55 comprising two packers 60 and at least one port 65, a fluid analyzer module 70, and a pumpout module 75. The apparatus 40 may also comprise a sample module 80 comprising one or more detachable sample bottles and/or other sample containers 85, and a conveyance terminal 90. The detachable containers 85 may receive and retain the formation fluid for subsequent testing at surface or a testing facility, and may thus be certified for highway and/or other transportation.

The probe 50 may be hydraulically or otherwise extendable from the apparatus 40 into contact with a sidewall of the wellbore, including for sealing contact therewith to establish fluid communication between the formation (penetrated by the wellbore) and one or more internal flow lines 97 spanning a substantial portion of the length of the apparatus 40. The probe 50 may also or instead be urged into contact with the wellbore sidewall via operation of one or more back-up pistons and/or apparatus (not shown) operable to urge the apparatus 40 towards the portion of the wellbore sidewall adjacent the probe 50.

The packer module 55 may comprise two packers 60, which may be independently and/or collectively operable to isolate a portion of the annulus formed between the wellbore sidewall and the apparatus 40, such as by mechanical, hydraulic, pneumatic, and/or other means for expanding and/or otherwise extending the packers 60 into contact with the wellbore sidewall. In certain embodiments, a tool and/or module comprising more or less than two packers, a different number of ports 65, and/or other features may replace the packer module 55.

The fluid analyzer module 70 may be operable to determine OD and/or various other parameters and information pertaining to the fluid flowing in the flowline 97. For example, the fluid analyzer module 70 may include a laser and/or other light source 71 and one or more detectors 72, which may collectively provide spectrometry capabilities. The fluid analyzer module 70 may include one or more other sensors 73 operable to determine other parameters pertaining to the fluid flow in the flowline 97, including for the determination of one or more geophysical, petrophysical, and/or other parameters of at least a portion of the formation F proximate the probe 50. For example, the sensors 73 may be operable to measure or detect one or more of pressure, temperature, density, viscosity, conductivity, composition, electric resistivity, dielectric constant, magnetic resonance relaxation time, nuclear radiation, and/or combinations thereof, although other types of sensors are also within the scope of the present disclosure. The sensors 73 may also or instead be located in other portions of the apparatus 40.

The detectors 72 may include one or more detector elements that may each measure the amount of light transmitted at a certain wavelength. For example, the detector elements may detect the light transmitted from the visible to near-infrared within a range of 1, 5, 10, 20, or more different wavelengths ranging between about 400 nm and about 2200 nm. However, other numbers of wavelengths (corresponding to the number of detector elements) and other ranges of wavelengths are also within the scope of the present disclosure. For example, OD of the formation fluid may be detected at a range of wavelengths, such as the near infrared (NIR) wavelength range of approximately 800-2500 nm, 1500-2050 nm, or 1600-1800 nm. Estimations of formation fluid properties according to one or more aspects of the present disclosure may utilize OD data collected at a single wavelength, at multiple wavelengths, over a range of wavelengths, and/or over multiple ranges of wavelengths.

The fluid analyzer module 70 may measure one or more optical characteristics (e.g., OD) of the formation fluid flowing through the flowline 97 and output optical spectra and/or other data representative of the detected optical characteristics. The optical characteristics may include OD of the formation fluid at each of the detected wavelengths and/or wavelength ranges. The OD may be a logarithmic measurement relating the intensity of light emitted from the light source 71 to the intensity of light detected by the detectors 72 at a certain wavelength or range of wavelengths. Each wavelength or wavelength range may correspond to a compositional component of the formation fluid. For example, each wavelength or wavelength range may pertain to a corresponding one of CO2, C1, C2, C3, C4, C5, and C6+, although other arrangements are also within the scope of the present disclosure.

Figure 12:
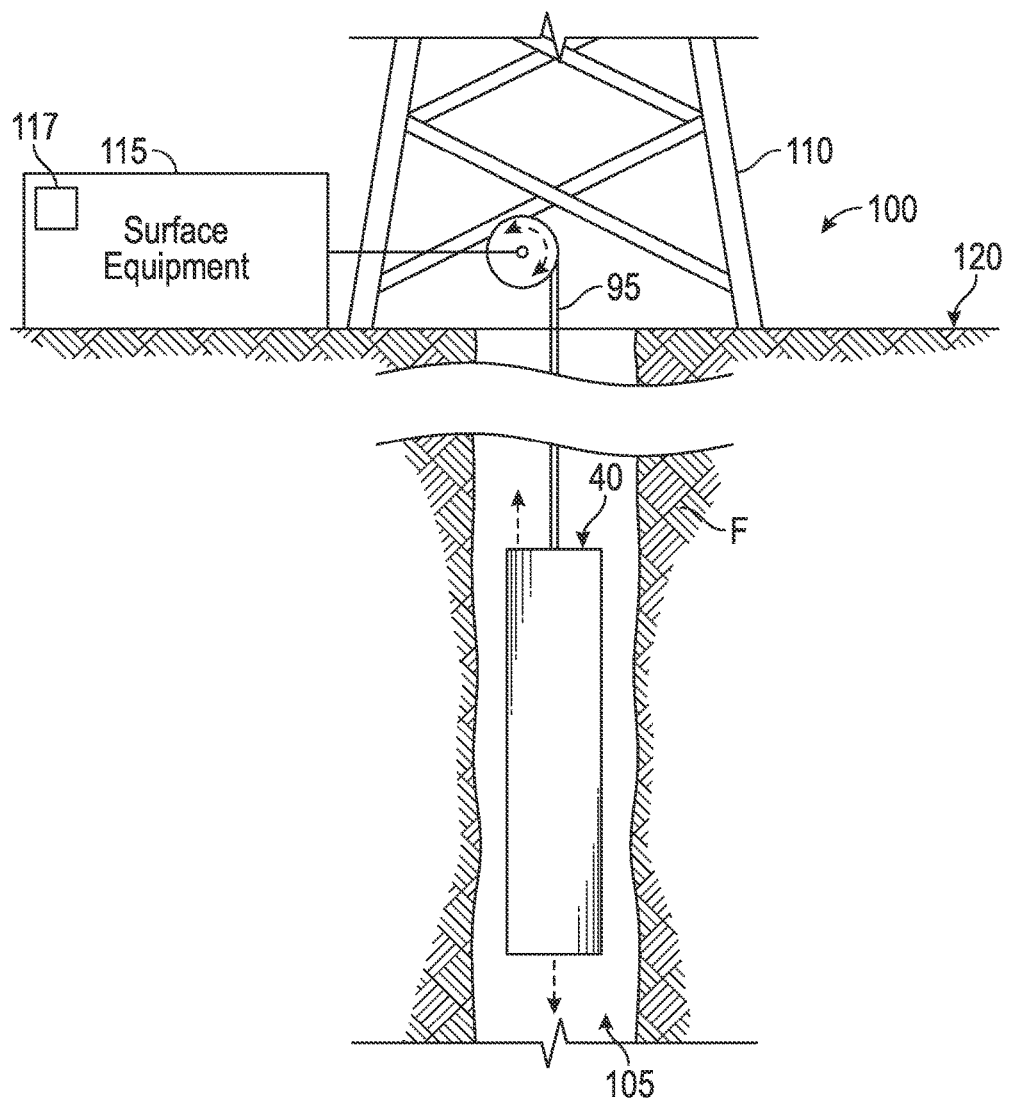
FIG. 12 is a schematic view of at least a portion of an example implementation of apparatus according to one or more aspects of the present disclosure.

The fluid analyzer module 70 may send optical spectra and/or other data representative of the measured optical characteristics to a processor 42 of the apparatus 40 and/or associated wellsite surface equipment (such as the surface equipment 115 shown in FIG. 12). In the context of the present disclosure, the term "processor" may refer to one or more processor components. The processor 42 is depicted in FIG. 11 as being a single processor disposed in the fluid analyzer module 70, but could instead be one or more processors disposed in one or more other locations within the apparatus 40. At least a portion of the processor (e.g., where multiple processors collectively operate together) may be located within the wellsite surface equipment.

The pumpout module 75 may include one or more electrical, mechanical, hydraulic, and/or other pumps 76 operable to pump fluid (liquid and/or gas) from the one or more probes 50 of the probe module 45 and/or from the one or more ports 65 of the packer module 55. Various valves and/or other hydraulic circuitry (not shown) may be operable to facilitate such fluid transfer in conjunction with the one or more flowlines 97. The one or more pumps 76 also may be operable to pump fluid to the one or more sample containers 85 of the sample module 80.

The conveyance terminal 90 may be operable to provide an interface between a conveyance means 95 and the remainder of the apparatus 40. For example, the conveyance means 95 may include a wireline (mono-cable, multi-conductor, and/or others), slickline, coiled tubing, wired drill pipe, or drill string, among others. The interface provided by the conveyance terminal 90 may be mechanical, electrical (e.g., power and/or data), hydraulic, pneumatic, and/or otherwise.

One or more other devices, tools, modules, and/or other apparatus 98 may be positioned below the dual-packer module 55. However, the scope of the present disclosure is not limited by the number and/or function of such additional apparatus 98, and such apparatus 98 may not be utilized in each implementation falling within the scope of the present disclosure.

The apparatus 40 shown in FIG. 11, among other implementations of formation tester/logging apparatus within the scope of the present disclosure, may be operable to measure pressures, collect samples, conduct well testing, and perform stress testing in open-hole and/or cased-hole conditions, among other functions. The goals of a particular logging run, among other parameters, may be utilized to determine the operational modules, tools, features, and/or functions of the selected toolstring. The DFA measurements obtained via utilization of an apparatus such as the apparatus 40 shown in FIG. 11, among others within the scope of the present disclosure, may be utilized to assess biodegradation and related parameters of an oil column and/or other formation according to one or more aspects described above.

FIG. 12 is a schematic view of an example implementation of a wellsite system 100 that may be employed onshore and/or offshore according to one or more aspects of the present disclosure, representing an example environment in which one or more aspects of the apparatus 40 shown in FIG. 11 may be implemented. As depicted in FIG. 12, an implementation of the apparatus 40 may be suspended from a platform, rig, derrick, and/or other wellsite structure 110 in a wellbore 105 formed in an oil column and/or other subterranean formation F. The apparatus 40 may be or comprise one or more tools, modules, and/or apparatus instead of or in addition to those described above and/or shown in FIG. 11, one or more of which may be or comprise an acoustic tool, a conveyance tool, a density tool, an electromagnetic (EM) tool, a formation evaluation tool, a magnetic resonance tool, a monitoring tool, a neutron tool, a nuclear tool, a photoelectric factor tool, a porosity tool, a reservoir characterization tool, a resistivity tool, a seismic tool, a surveying tool, and/or a telemetry tool, although other downhole tools are also within the scope of the present disclosure.

The apparatus 40 may be deployed from the wellsite structure 110 into the wellbore 105 via the conveyance means 95. As the apparatus 40 operates, outputs of various numbers and/or types from the apparatus 40 and/or components thereof may be sent to a logging and control system and/or other surface equipment 115 at surface 120, and/or may be stored in various numbers and/or types of memory for subsequent recall and/or processing after the apparatus 40 is retrieved to surface 120. The surface equipment 115 may comprise a controller and/or other processor 117 having an interface operable to receive commands from a surface operator.

The processor 42 of the apparatus 40 and/or the processor 117 of the surface equipment 115 may be collectively operable to perform at least a portion of a method according to one or more aspects of the present disclosure. For example, the processor 42 of the apparatus 40 and/or the processor 117 of the surface equipment 115 may be operable to control the probe 50 and/or components for the extraction of fluid samples from the formation F, such as via control of the pumping rate of pump 76. The processor 42 of the apparatus 40 and/or the processor 117 of the surface equipment 115 may be further operable to analyze and/or process data obtained from the detectors 72 and/or the sensors 73, store measurements or processed data, and/or communicate measurements or processed data for subsequent analysis.

Figure 13:
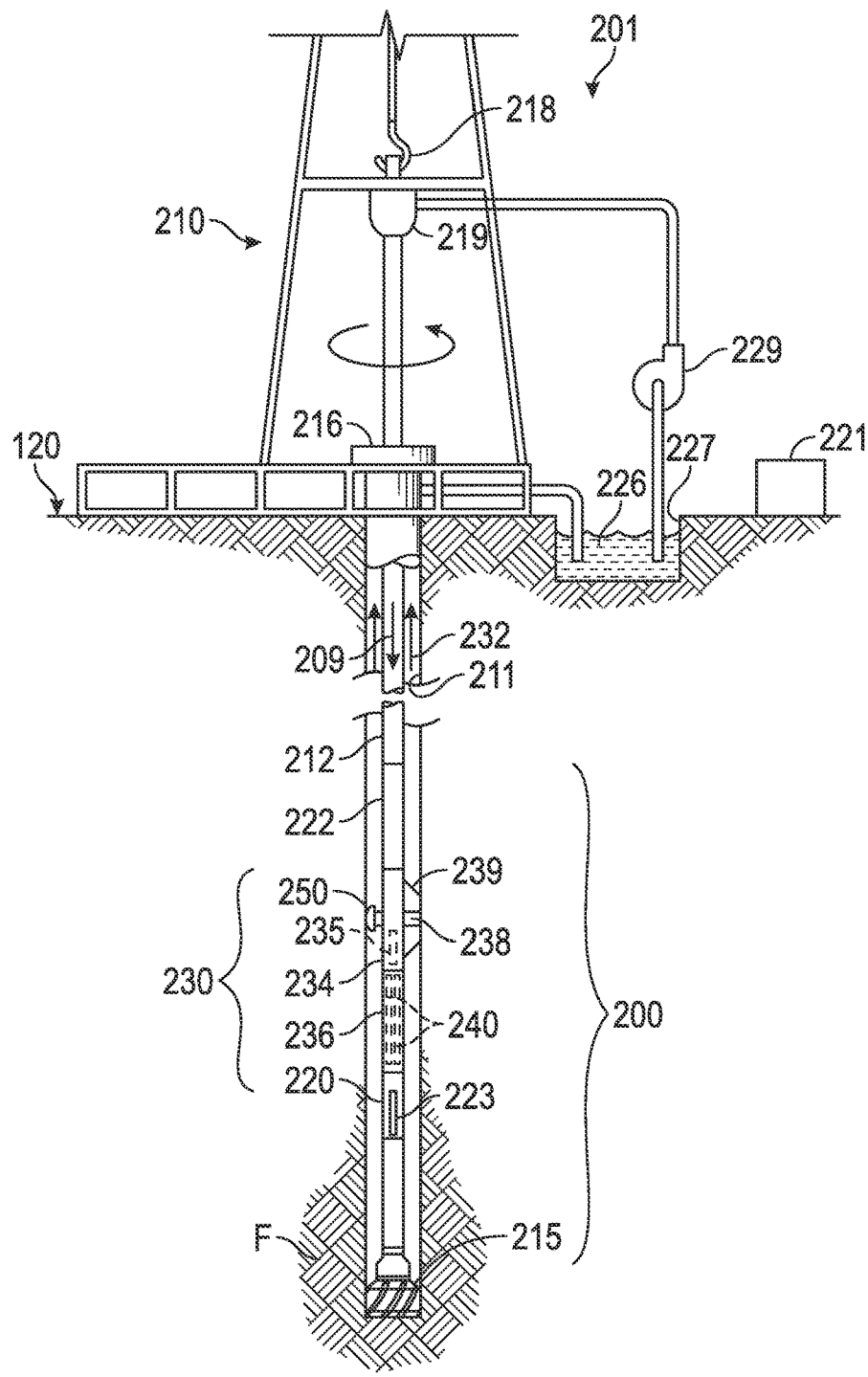
FIG. 13 is a schematic view of at least a portion of an example implementation of apparatus according to one or more aspects of the present disclosure.

While at least portions of the above description, including one or more aspects depicted in one or more of FIGS. 11 and 12, are presented in the context of a wireline formation tester, one or more such aspects may also be applicable or readily adaptable to while-drilling and other drill string conveyed apparatus. For example, FIG. 13 is a schematic view of at least a portion of apparatus that may be utilized, or adapted for utilization with, one or more aspects of the present disclosure. Depicted components include a wellsite system 201, a rig 210, and a downhole tool 200 suspended from the rig 210 and into a wellbore 211 via a drill string 212. The downhole tool 200, or a bottom hole assembly ("BHA") comprising the downhole tool 200, comprises or is coupled to a drill bit 215 at its lower end that is used to advance the downhole tool into the formation F and form the wellbore. The drillstring 212 may be rotated by a rotary table 216 that engages a kelly at the upper end of the drillstring. The drillstring 212 is suspended from a hook 218 attached to a traveling block (not shown) and a rotary swivel 219 that permits rotation of the drillstring relative to the hook.

The rig 210 is depicted as a land-based platform and derrick assembly utilized to form the wellbore 211 by rotary drilling in a manner that is well known. A person having ordinary skill in the art will appreciate, however, that one or more aspects of the present disclosure may also find use in other downhole applications, such as rotary drilling, and is not limited to land-based rigs.

Drilling fluid or mud 226 is stored in a pit 227 formed at the well site. A pump 229 delivers drilling fluid 226 to the interior of the drillstring 212 via a port in the swivel 219, inducing the drilling fluid to flow downward through the drillstring 212, as indicated in FIG. 13 by directional arrow 209. The drilling fluid 226 exits the drillstring 212 via ports in the drill bit 215, and then circulates upward through the annulus defined between the outside of the drillstring 212 and the wall of the wellbore 211, as indicated by directional arrows 232. In this manner, the drilling fluid 226 lubricates the drill bit 215 and carries formation cuttings up to the surface 120 as it is returned to the pit 227 for recirculation.

The downhole tool 200 and/or BHA may be positioned near the drill bit 215 (e.g., within several drill collar lengths from the drill bit 215). The downhole tool 200 comprises various components with various capabilities, such as measuring, processing, and storing information. A telemetry device 222 is also provided for communicating with a surface unit 221.

The downhole tool 200 also comprises a sampling system 230 that includes a fluid communication module 234 and a sample module 236 which may be individually or collectively housed in one or more drill collars for performing various formation evaluation and/or sampling functions. The fluid communication module 234 and sample module 236 may be operationally similar to the probe module 45 and sample module 80 described above with respect to FIG. 11, although perhaps ruggedized for drilling applications. The fluid communication module 234 may be positioned adjacent the sample module 236, and may comprise one or more pumps 235, gauges, sensors, and/or other devices that may also be utilized for downhole sampling and/or testing.

The downhole tool 200 shown in FIG. 13 is depicted as having a modular construction with specific components in certain modules. However, the downhole tool 200 may be unitary, or select portions thereof may be modular. The modules and/or the components therein may be positioned in a variety of configurations throughout the downhole tool 200.

The fluid communication module 234 may comprise a fluid communication device 238, which may be positioned in a stabilizer blade or rib 239. The fluid communication device 238 may be or comprise one or more probes, inlets, and/or other means for receiving sampled fluid from the formation F and/or the wellbore 211. The fluid communication device 238 also comprises a flowline (not shown but operationally similar to the flowline 97 shown in FIG. 11) extending into the downhole tool 200 for passing fluids therethrough. The fluid communication device 238 may be movable between extended and retracted positions for selectively engaging a wall of the wellbore 211 and acquiring one or more fluid samples from the formation 130. The fluid communication module 210 may also comprise a back-up piston 250 operable to assist in positioning the fluid communication device 227 against the wall of the wellbore 211.

The sample module 236 comprises one or more sample chambers 240. The sample chambers 240 may each be detachable from the sample module 236 at the surface 120, and may be certified for subsequent highway and/or other transportation.

The downhole tool 200 may also comprise a downhole control system 220 operable to communicate with surface equipment 221. The downhole control system 220 may include one or more processors 223 and/or other apparatus configured to control the telemetry device 222, the sampling system 430, and/or other modules, components, and/or features for the extraction and/or analysis of fluid samples from the formation 130.

A person having ordinary skill in the art will recognize that various instances of the apparatus, components, and/or other features depicted in FIG. 13 may be analogous and/or substantially similar in name, operation, and/or function to corresponding features depicted one or more of FIGS. 11 and 12 and/or otherwise described above.

Figure 14:
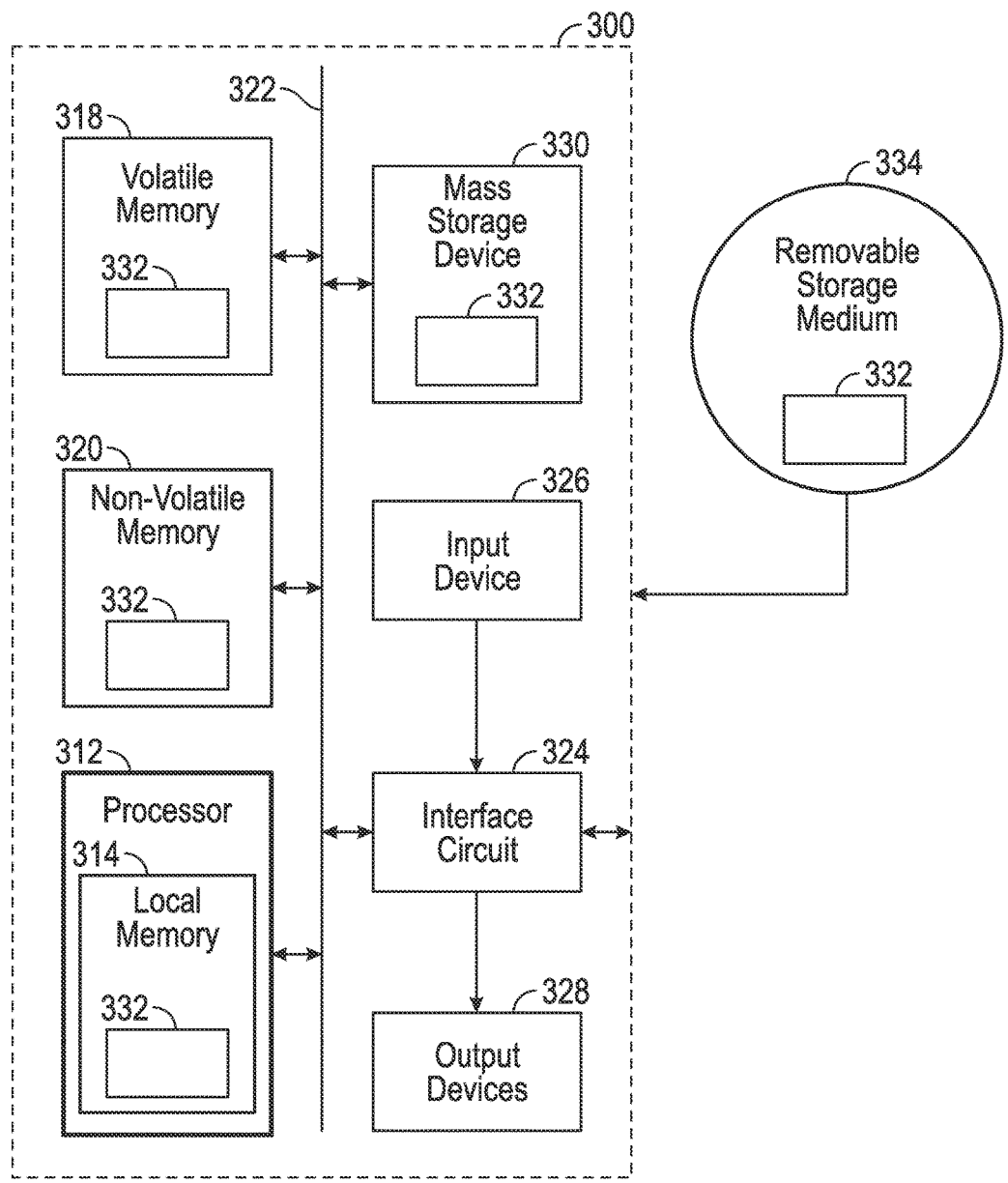
FIG. 14 is a schematic view of at least a portion of an example implementation of apparatus according to one or more aspects of the present disclosure.

FIG. 14 is a schematic view of at least a portion of apparatus according to one or more aspects of the present disclosure. The apparatus is or comprises a processing system 300 that may execute example machine-readable instructions to implement at least a portion of one or more of the methods and/or processes described herein, and/or to implement at least a portion of one or more of the example downhole modules, tools, tool strings, components, processors, controllers, and/or other apparatus described herein. The processing system 300 may be or comprise, for example, one or more processors, controllers, special-purpose computing devices, servers, personal computers, and/or other types of computing devices. Moreover, while it is possible that the processing system 300 shown in FIG. 14 is implemented within downhole apparatus, such as in the form of the processor 42 shown in FIG. 11 and/or the processor(s) 223 or control system 220 shown in FIG. 13, and/or other downhole apparatus, it is also contemplated that one or more components and/or functions of the processing system 300 may be implemented in wellsite surface equipment, perhaps including at least a portion of the surface equipment 115 depicted in FIG. 12, the surface equipment 221 depicted in FIG. 13, and/or other surface equipment.

The processing system 300 may comprise a processor 312 such as, for example, a general-purpose programmable processor. The processor 312 may comprise a local memory 314, and may execute coded instructions 332 present in the local memory 314 and/or another memory device. The processor 312 may execute, among other things, machine-readable instructions or programs to implement the methods and/or processes described herein. The programs stored in the local memory 314 may include program instructions or computer program code that, when executed by an associated processor, enable surface equipment and/or downhole controller and/or control system to perform tasks as described herein. The processor 312 may be, comprise, or be implemented by one or a plurality of processors of various types suitable to the local application environment, and may include one or more of general-purpose computers, special purpose computers, microprocessors, digital signal processors ("DSPs"), field-programmable gate arrays ("FPGAs"), application-specific integrated circuits ("ASICs"), and processors based on a multi-core processor architecture, as non-limiting examples. Of course, other processors from other families are also appropriate.

The processor 312 may be in communication with a main memory, such as may include a volatile memory 318 and a non-volatile memory 320, perhaps via a bus 322 and/or other communication means. The volatile memory 318 may be, comprise, or be implemented by random access memory (RAM), static random access memory (SRAM), synchronous dynamic random access memory (SDRAM), dynamic random access memory (DRAM), RAMBUS dynamic random access memory (RDRAM) and/or other types of random access memory devices. The non-volatile memory 320 may be, comprise, or be implemented by read only memory, flash memory and/or other types of memory devices. One or more memory controllers (not shown) may control access to the volatile memory 318 and/or the non-volatile memory 320.

The processing system 300 may also comprise an interface circuit 324. The interface circuit 324 may be, comprise, or be implemented by various types of standard interfaces, such as an Ethernet interface, a universal serial bus (USB), a third generation input/output (3GIO) interface, a wireless interface, and/or a cellular interface, among others. The interface circuit 324 may also comprise a graphics driver card. The interface circuit 324 may also comprise a communication device such as a modem or network interface card to facilitate exchange of data with external computing devices via a network (e.g., Ethernet connection, digital subscriber line ("DSL"), telephone line, coaxial cable, cellular telephone system, satellite, etc.).

One or more input devices 326 may be connected to the interface circuit 324. The input device(s) 326 may permit a user to enter data and commands into the processor 312. The input device(s) 326 may be, comprise, or be implemented by, for example, a keyboard, a mouse, a touchscreen, a track-pad, a trackball, an isopoint, and/or a voice recognition system, among others.

One or more output devices 328 may also be connected to the interface circuit 324. The output devices 328 may be, comprise, or be implemented by, for example, display devices (e.g., a liquid crystal display or cathode ray tube display (CRT), among others), printers, and/or speakers, among others.

The processing system 300 may also comprise one or more mass storage devices 330 for storing machine-readable instructions and data. Examples of such mass storage devices 330 include floppy disk drives, hard drive disks, compact disk (CD) drives, and digital versatile disk (DVD) drives, among others. The coded instructions 332 may be stored in the mass storage device 330, the volatile memory 318, the non-volatile memory 320, the local memory 314, and/or on a removable storage medium 334, such as a CD or DVD. Thus, the modules and/or other components of the processing system 300 may be implemented in accordance with hardware (embodied in one or more chips including an integrated circuit such as an application specific integrated circuit), or may be implemented as software or firmware for execution by a processor. In particular, in the case of firmware or software, the embodiment can be provided as a computer program product including a computer readable medium or storage structure embodying computer program code (i.e., software or firmware) thereon for execution by the processor.

Figure 15:
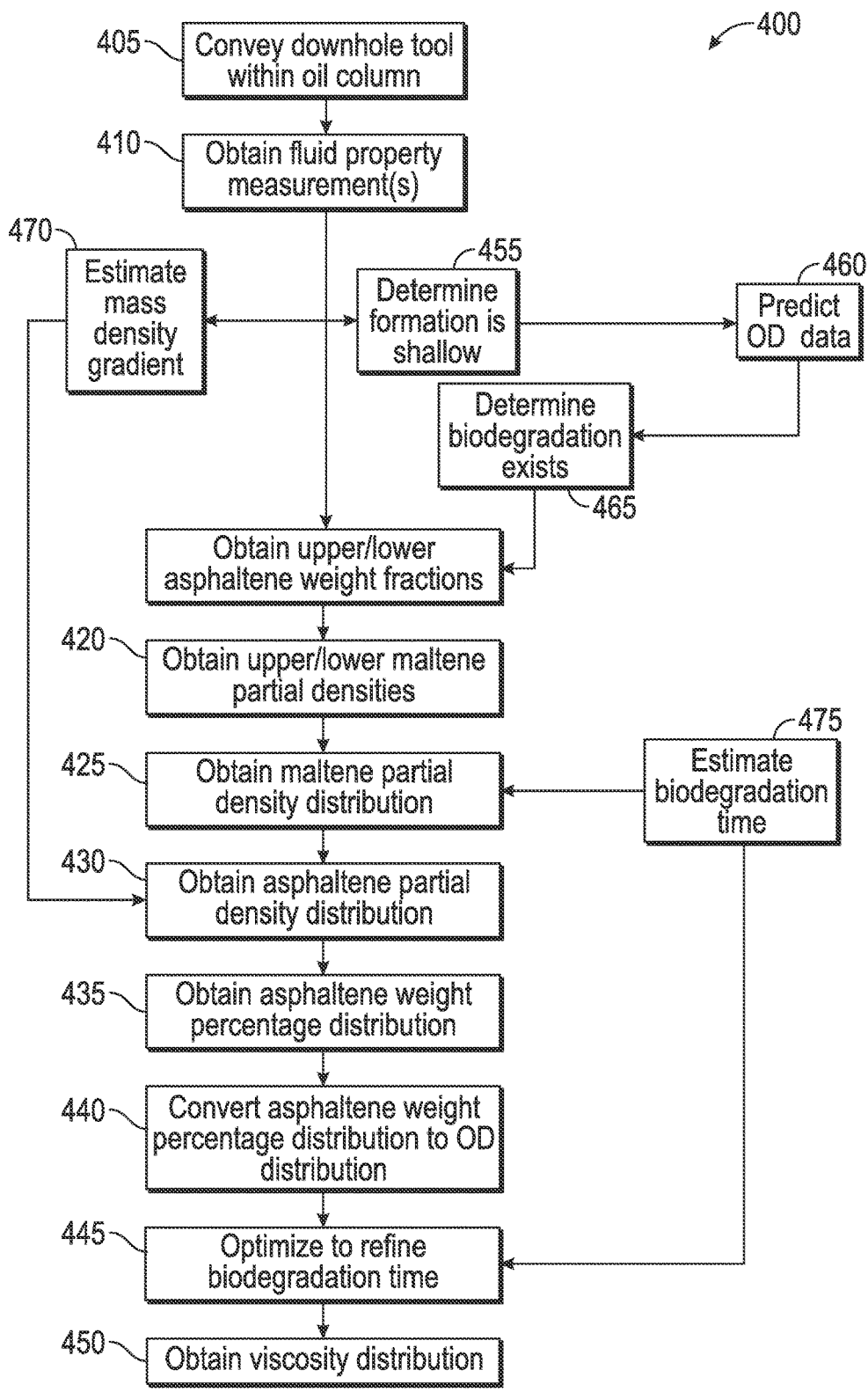
FIG. 15 is a flow-chart diagram of at least a portion of an example implementation of a method according to one or more aspects of the present disclosure.

It follows from the description above that the present disclosure introduces aspects by which fluid properties of a biodegraded oil column may be assessed. FIG. 15 is a flow-chart diagram of an example implementation of such a method (400) for assessing fluid properties of a biodegraded oil column. The method (400) may be performed in conjunction with the apparatus 40 shown in FIG. 11, the wellsite system 100 shown in FIG. 12, the wellsite system 201 shown in FIG. 13, the processing system 300 shown in FIG. 14, various combinations of the components thereof, and/or other apparatus within the scope of the present disclosure.

The method (400) includes conveying (405) a downhole tool within a wellbore that extends from a wellsite surface into a subterranean oil column. The downhole tool may be, or may be substantially similar to at least a portion of, the apparatus 40 shown in FIGS. 11 and 12, the downhole tool 200 shown in FIG. 13, and/or the processing system 300 shown in FIG. 14. The downhole tool is in communication with surface equipment located at the wellsite surface. The surface equipment may be, or may be substantially similar to at least a portion of, the surface equipment 115 shown in FIG. 12, the surface equipment 221 shown in FIG. 13, and/or the processing system 300 shown in FIG. 14.

The method (400) also includes operating the downhole tool and/or the surface equipment to obtain (410) one or more fluid property measurements of fluid obtained from the oil column at each of a plurality of depths within the oil column. For example, the downhole tool and/or the surface equipment may be operated to measure OD of the fluid at each depth. However, the obtained (410) fluid property measurements may also comprise mass density, temperature, and/or other properties of the oil column fluid at each depth.

The method (400) also includes operating the downhole tool and/or the surface equipment to obtain (415) upper and lower asphaltene weight fractions of fluid proximate respective ends of the oil column based on the measured OD. The upper and lower asphaltene weight fractions may be obtained (415) based on the OD measured (410) proximate the respective oil column ends. Obtaining (415) the upper and lower asphaltene weight fractions may utilize a predetermined correlation between asphaltene weight fraction and OD. The predetermined correlation between asphaltene weight fraction and OD may be a linear relationship determined empirically from data obtained from other wellbores, laboratory data, or other data obtained prior to conveying the downhole tool within the wellbore.

The method (400) also includes operating the downhole tool and/or the surface equipment to obtain (420) upper and lower maltene partial densities of the fluid proximate the respective oil column ends based on the respective upper and lower asphaltene weight fractions. The upper and lower maltene partial densities may be obtained (420) based on the obtained (415) upper and lower asphaltene weight fractions, respectively, and the mass density measured (410) proximate the respective oil column ends.

The method (400) also includes operating the downhole tool and/or the surface equipment to obtain (425) a maltene partial density distribution along depth within the oil column. Obtaining (425) the maltene partial density distribution may utilize the obtained (420) upper and lower maltene partial densities and a predetermined diffusion model.

The method (400) also includes operating the downhole tool and/or the surface equipment to obtain (430) an asphaltene partial density distribution along depth within the oil column. Obtaining (430) the asphaltene partial density distribution may be based on the obtained (425) maltene partial density distribution and a mass density gradient estimated with respect to depth within the oil column.

The method (400) also includes operating the downhole tool and/or the surface equipment to obtain (435) an asphaltene weight percentage distribution along depth within the oil column. Obtaining (435) the asphaltene weight percentage distribution may be based on the obtained (430) asphaltene partial density distribution and the estimated mass density gradient.

The method (400) also includes operating the downhole tool and/or the surface equipment to convert (440) the asphaltene weight percentage distribution to an OD distribution. Converting (440) the asphaltene weight percentage distribution to the OD distribution may utilize a predetermined correlation between asphaltene weight fraction and OD.

The method (400) also includes operating the downhole tool and/or the surface equipment to perform (445) an optimization process to reduce differences between the converted (440) OD distribution and the measured (410) OD data to within a predetermined range and refine a biodegradation time of the predetermined diffusion model.

The method (400) may also include operating the downhole tool and/or the surface equipment to obtain (450) a viscosity distribution along depth within the oil column based on the optimized OD distribution.

The method (400) may also include operating the downhole tool and/or the surface equipment to determine (455) that the oil column is a shallow formation. For example, a shallow formation may have a maximum depth below the wellsite surface of about 1500 meters.

The method (400) may also include operating the downhole tool and/or the surface equipment to generate (460) predicted OD data based on a substantial lack of biodegradation within the oil column. Generating (460) the predicted OD data may be based on a predetermined relationship between OD and/or asphaltene content relative to depth within the oil column assuming substantially no biodegradation exists. For example, as described above, the predetermined relationship between OD and/or asphaltene content relative to depth within the oil column may be based on or utilize the FHZ EoS.

The method (400) may also include operating the downhole tool and/or the surface equipment to determine (465) that the oil column has experienced biodegradation based on the measured (410) temperature data, the shallow formation determination (455), and a comparison of the measured OD data to predicted OD data.

The method (400) may also include operating the downhole tool and/or the surface equipment to estimate (470) the mass density gradient with respect to depth within the oil column. For example, estimating (470) the mass density gradient may entail fitting or interpolating the measured (410) mass density data to a polynomial or other function.

The method (400) may also include operating the downhole tool and/or the surface equipment to estimate (475) the biodegradation time. For example, estimating (475) the biodegradation time may utilize a fitting process and Fick's second law.

In view of the entirety of the present disclosure, including the figures and the claims, a person having ordinary skill in the art will readily recognize that the present disclosure introduces a method of modeling optical density (OD), asphaltene, and viscosity gradients in a biodegraded oil column, comprising: conveying a downhole tool within a wellbore, wherein the wellbore extends from a wellsite surface into a subterranean oil column, and wherein the downhole tool is in communication with surface equipment located at the wellsite surface; and operating at least one of the downhole tool and the surface equipment to: (a) measure temperature, mass density, and optical density (OD) of fluid in the oil column at each of a plurality of depths within the oil column; (b) compare the measured OD data to predicted OD data; (c) determine that the oil column is a shallow formation; (d) determine that the oil column has experienced biodegradation based on the measured temperature data, the OD data comparison, and the shallow formation determination; (e) estimate a mass density gradient with respect to depth within the oil column; (f) obtain an upper asphaltene weight fraction of fluid proximate a top of the oil column based on the OD measured proximate the top of the oil column utilizing a predetermined correlation between asphaltene weight fraction and OD; (g) obtain an upper maltene partial density of the fluid proximate the top of the oil column based on the upper asphaltene weight fraction and the mass density measured proximate the top of the oil column; (h) obtain a lower asphaltene weight fraction of fluid proximate a bottom of the oil column based on the OD measured proximate the bottom of the oil column utilizing the predetermined correlation between asphaltene weight fraction and OD; (i) obtain a lower maltene partial density of the fluid proximate the bottom of the oil column based on the lower asphaltene weight fraction and the mass density measured proximate the bottom of the oil column; (j) select a biodegradation time to be utilized with a predetermined diffusion model; (k) obtain a maltene partial density distribution with respect to depth within the oil column, based on the upper and lower maltene partial densities and the depths at which the OD data are measured, and utilizing the predetermined diffusion model; (l) obtain an asphaltene partial density distribution with respect to depth within the oil column based on the mass density gradient and the maltene partial density distribution; (m) obtain an asphaltene weight percentage distribution with respect to depth within the oil column based on the asphaltene partial density distribution and the mass density gradient; (n) convert the asphaltene weight percentage distribution to an OD distribution utilizing the predetermined correlation between asphaltene weight fraction and OD; (o) perform an optimization process to adjust the biodegradation time and thus minimize differences between the OD distribution and the measured OD data to within a predetermined range; and (p) obtain a viscosity distribution with respect to depth within the oil column based on the OD distribution.

In element (b), the predicted OD data may be based on a substantial lack of biodegradation within the oil column.

Such method may further comprise operating at least one of the downhole tool and the surface equipment to, prior to element (b), generate the predicted OD data based on a predetermined relationship between OD and depth within the oil column assuming no biodegradation exists. The predetermined relationship between OD and depth within the oil column may utilize the FHZ equation of state.

Such method may further comprise operating at least one of the downhole tool and the surface equipment to, prior to element (b), generate the predicted OD data based on a predetermined relationship between asphaltene content and depth within the oil column assuming no biodegradation exists. The predetermined relationship between asphaltene content and depth within the oil column may utilize the FHZ equation of state.

Operating at least one of the downhole tool and the surface equipment to estimate the mass density gradient with respect to depth within the oil column may utilize fitting or interpolating the measured mass density data to a polynomial or other function.

The shallow formation may have a maximum depth below the wellsite surface of about 1500 meters.

The predetermined correlation between asphaltene weight fraction and OD may be a linear relationship determined empirically from data obtained from other wellbores, laboratory data, or other data obtained prior to conveying the downhole tool within the wellbore.

Operating at least one of the downhole tool and the surface equipment to select a biodegradation time to be utilized with the predetermined diffusion model may utilize a fitting process and Fick's second law.

The present disclosure also introduces a system for modeling optical density (OD), asphaltene, and viscosity gradients in a biodegraded oil column, comprising: a downhole tool conveyable within a wellbore, wherein the wellbore extends from a wellsite surface into a subterranean oil column; and surface equipment located at the wellsite surface and in communication with the downhole tool; wherein the downhole tool and the surface equipment are collectively operable to: (a) measure temperature, mass density, and optical density (OD) of fluid in the oil column at each of a plurality of depths within the oil column; (b) compare the measured OD data to predicted OD data; (c) determine that the oil column is a shallow formation; (d) determine that the oil column has experienced biodegradation based on the measured temperature data, the OD data comparison, and the shallow formation determination; (e) estimate a mass density gradient with respect to depth within the oil column; (f) obtain an upper asphaltene weight fraction of fluid proximate a top of the oil column based on the OD measured proximate the top of the oil column utilizing a predetermined correlation between asphaltene weight fraction and OD; (g) obtain an upper maltene partial density of the fluid proximate the top of the oil column based on the upper asphaltene weight fraction and the mass density measured proximate the top of the oil column; (h) obtain a lower asphaltene weight fraction of fluid proximate a bottom of the oil column based on the OD measured proximate the bottom of the oil column utilizing the predetermined correlation between asphaltene weight fraction and OD; (i) obtain a lower maltene partial density of the fluid proximate the bottom of the oil column based on the lower asphaltene weight fraction and the mass density measured proximate the bottom of the oil column; (j) select a biodegradation time to be utilized with a predetermined diffusion model; (k) obtain a maltene partial density distribution with respect to depth within the oil column, based on the upper and lower maltene partial densities and the depths at which the OD data are measured, and utilizing the predetermined diffusion model; (l) obtain an asphaltene partial density distribution with respect to depth within the oil column based on the mass density gradient and the maltene partial density distribution; (m) obtain an asphaltene weight percentage distribution with respect to depth within the oil column based on the asphaltene partial density distribution and the mass density gradient; (n) convert the asphaltene weight percentage distribution to an OD distribution utilizing the predetermined correlation between asphaltene weight fraction and OD; (o) perform an optimization process to adjust the biodegradation time and thus minimize differences between the OD distribution and the measured OD data to within a predetermined range; and (p) obtain a viscosity distribution with respect to depth within the oil column based on the OD distribution.

In element (b), the predicted OD data may be based on a substantial lack of biodegradation within the oil column.

The downhole tool and the surface equipment may collectively be further operable to, prior to element (b), generate the predicted OD data based on a predetermined relationship between OD and depth within the oil column assuming no biodegradation exists. The predetermined relationship between OD and depth within the oil column may utilize the FHZ equation of state.

The downhole tool and the surface equipment may collectively be further operable to, prior to element (b), generate the predicted OD data based on a predetermined relationship between asphaltene content and depth within the oil column assuming no biodegradation exists. The predetermined relationship between asphaltene content and depth within the oil column may utilize the FHZ equation of state.

The downhole tool and the surface equipment may collectively be further operable to estimate the mass density gradient with respect to depth within the oil column by fitting or interpolating the measured mass density data to a polynomial or other function.

The present disclosure also introduces a computer program product, comprising: a non-transitory, computer-readable medium; and instructions recorded on the non-transitory, computer-readable medium for operating a downhole tool positioned within a wellbore and surface equipment in communication with the downhole tool to: (a) measure temperature, mass density, and optical density (OD) of fluid in an oil column penetrated by the wellbore at each of a plurality of depths within the oil column; (b) compare the measured OD data to predicted OD data; (c) determine that the oil column is a shallow formation; (d) determine that the oil column has experienced biodegradation based on the measured temperature data, the OD data comparison, and the shallow formation determination; (e) estimate a mass density gradient with respect to depth within the oil column; (f) obtain an upper asphaltene weight fraction of fluid proximate a top of the oil column based on the OD measured proximate the top of the oil column utilizing a predetermined correlation between asphaltene weight fraction and OD; (g) obtain an upper maltene partial density of the fluid proximate the top of the oil column based on the upper asphaltene weight fraction and the mass density measured proximate the top of the oil column; (h) obtain a lower asphaltene weight fraction of fluid proximate a bottom of the oil column based on the OD measured proximate the bottom of the oil column utilizing the predetermined correlation between asphaltene weight fraction and OD; (i) obtain a lower maltene partial density of the fluid proximate the bottom of the oil column based on the lower asphaltene weight fraction and the mass density measured proximate the bottom of the oil column; (j) select a biodegradation time to be utilized with a predetermined diffusion model; (k) obtain a maltene partial density distribution with respect to depth within the oil column, based on the upper and lower maltene partial densities and the depths at which the OD data are measured, and utilizing the predetermined diffusion model; (l) obtain an asphaltene partial density distribution with respect to depth within the oil column based on the mass density gradient and the maltene partial density distribution; (m) obtain an asphaltene weight percentage distribution with respect to depth within the oil column based on the asphaltene partial density distribution and the mass density gradient; (n) convert the asphaltene weight percentage distribution to an OD distribution utilizing the predetermined correlation between asphaltene weight fraction and OD; (o) perform an optimization process to adjust the biodegradation time and thus minimize differences between the OD distribution and the measured OD data to within a predetermined range; and (p) obtain a viscosity distribution with respect to depth within the oil column based on the OD distribution.

In element (b), the predicted OD data may be based on a substantial lack of biodegradation within the oil column.

The instructions recorded on the non-transitory, computer-readable medium may further be for operating the downhole tool and surface equipment to, prior to element (b), generate the predicted OD data based on a predetermined relationship between OD, asphaltene content, and depth within the oil column, assuming no biodegradation exists, wherein the predetermined relationship between OD, asphaltene content, and depth within the oil column utilizes the FHZ equation of state.

The present disclosure also introduces a method comprising: conveying a downhole tool within a wellbore, wherein the wellbore extends from a wellsite surface into a subterranean oil column, and wherein the downhole tool is in communication with surface equipment located at the wellsite surface; and operating at least one of the downhole tool and the surface equipment to: measure OD of fluid at a plurality of depths within the oil column; obtain upper and lower asphaltene weight fractions of fluid proximate respective ends of the oil column based on the measured OD; obtain upper and lower maltene partial densities of the fluid proximate the respective oil column ends based on the respective upper and lower asphaltene weight fractions;

obtain a maltene partial density distribution along depth within the oil column utilizing the upper and lower maltene partial densities and a predetermined diffusion model; obtain an asphaltene partial density distribution along depth within the oil column based on the maltene partial density distribution and a mass density gradient estimated with respect to depth within the oil column; obtain an asphaltene weight percentage distribution along depth within the oil column based on the asphaltene partial density distribution and the mass density gradient; convert the asphaltene weight percentage distribution to an OD distribution utilizing a predetermined correlation between asphaltene weight fraction and OD; and perform an optimization process to reduce differences between the OD distribution and the measured OD data to within a predetermined range and refine a biodegradation time of the predetermined diffusion model.

The method may further comprise operating at least one of the downhole tool and the surface equipment to obtain a viscosity distribution along depth within the oil column based on the optimized OD distribution.

The upper and lower asphaltene weight fractions may be obtained based on the OD measured proximate the respective oil column ends. The upper and lower asphaltene weight fractions may be obtained utilizing the predetermined correlation between asphaltene weight fraction and OD.

The method may further comprise operating at least one of the downhole tool and the surface equipment to measure mass density of the fluid at the plurality of depths, and the upper and lower maltene partial densities may be obtained based on the respective upper and lower asphaltene weight fractions and the mass density measured proximate the respective oil column ends.

The method may further comprise operating at least one of the downhole tool and the surface equipment to measure temperature of the fluid at the plurality of depths. Such method may further comprise operating at least one of the downhole tool and the surface equipment to determine that the oil column is a shallow formation having a maximum depth below the wellsite surface of about 1500 meters. Such method may further comprise operating at least one of the downhole tool and the surface equipment to determine that the oil column has experienced biodegradation based on the measured temperature data, the shallow formation determination, and a comparison of the measured OD data to predicted OD data. The predicted OD data may be based on a substantial lack of biodegradation within the oil column. Such method may further comprise operating at least one of the downhole tool and the surface equipment to generate the predicted OD data based on a predetermined relationship between OD and depth within the oil column assuming substantially no biodegradation exists. Such method may further comprise operating at least one of the downhole tool and the surface equipment to generate the predicted OD data based on a predetermined relationship between asphaltene content and depth within the oil column assuming substantially no biodegradation exists.

The method may further comprise operating at least one of the downhole tool and the surface equipment to estimate the mass density gradient with respect to depth within the oil column by fitting or interpolating the measured mass density data to a polynomial or other function.

The predetermined correlation between asphaltene weight fraction and OD may be a linear relationship determined empirically from data obtained from other wellbores, laboratory data, or other data obtained prior to conveying the downhole tool within the wellbore.

The method may further comprise operating at least one of the downhole tool and the surface equipment to estimate the biodegradation time utilizing a fitting process and Fick's second law.

The present disclosure also introduces a system comprising: a downhole tool conveyable within a wellbore, wherein the wellbore extends from a wellsite surface into a subterranean oil column; and surface equipment located at the wellsite surface and in communication with the downhole tool; wherein the downhole tool and the surface equipment are collectively operable to: measure OD of fluid at a plurality of depths within the oil column; obtain upper and lower asphaltene weight fractions of fluid proximate respective ends of the oil column based on the measured OD; obtain upper and lower maltene partial densities of the fluid proximate the respective oil column ends based on the respective upper and lower asphaltene weight fractions; obtain a maltene partial density distribution along depth within the oil column utilizing the upper and lower maltene partial densities and a predetermined diffusion model; obtain an asphaltene partial density distribution along depth within the oil column based on the maltene partial density distribution and a mass density gradient estimated with respect to depth within the oil column; obtain an asphaltene weight percentage distribution along depth within the oil column based on the asphaltene partial density distribution and the mass density gradient; convert the asphaltene weight percentage distribution to an OD distribution utilizing a predetermined correlation between asphaltene weight fraction and OD; and perform an optimization process to reduce differences between the OD distribution and the measured OD data to within a predetermined range and refine a biodegradation time of the predetermined diffusion model.

The upper and lower asphaltene weight fractions may be obtained based on the OD measured proximate the respective oil column ends. The upper and lower asphaltene weight fractions may be obtained utilizing the predetermined correlation between asphaltene weight fraction and OD. The predicted OD data may be based on a substantial lack of biodegradation within the oil column. The predetermined correlation between asphaltene weight fraction and OD may be a linear relationship determined empirically from data obtained from other wellbores, laboratory data, or other data obtained prior to conveying the downhole tool within the wellbore.

The downhole tool and the surface equipment may collectively be further operable to: measure mass density of the fluid at the plurality of depths, wherein the upper and lower maltene partial densities are obtained based on the respective upper and lower asphaltene weight fractions and the mass density measured proximate the respective oil column ends; measure temperature of the fluid at the plurality of depths; determine that the oil column is a shallow formation having a maximum depth below the wellsite surface of about 1500 meters; determine that the oil column has experienced biodegradation based on the measured temperature data, the shallow formation determination, and a comparison of the measured OD data to predicted OD data; generate the predicted OD data based on a predetermined relationship between OD or asphaltene content and depth within the oil column assuming no biodegradation exists; estimate the mass density gradient with respect to depth within the oil column by fitting or interpolating the measured mass density data to a polynomial or other function; estimate the biodegradation time utilizing a fitting process and Fick's second law; and/or obtain a viscosity distribution along depth within the oil column based on the optimized OD distribution.

The present disclosure also introduces a computer program product comprising: a non-transitory, computer-readable medium; and instructions recorded on the non-transitory, computer-readable medium for operating a downhole tool positioned within a wellbore and surface equipment in communication with the downhole tool to: measure OD of fluid at a plurality of depths within the oil column; obtain upper and lower asphaltene weight fractions of fluid proximate respective ends of the oil column based on the measured OD; obtain upper and lower maltene partial densities of the fluid proximate the respective oil column ends based on the respective upper and lower asphaltene weight fractions; obtain a maltene partial density distribution along depth within the oil column utilizing the upper and lower maltene partial densities and a predetermined diffusion model; obtain an asphaltene partial density distribution along depth within the oil column based on the maltene partial density distribution and a mass density gradient estimated with respect to depth within the oil column; obtain an asphaltene weight percentage distribution along depth within the oil column based on the asphaltene partial density distribution and the mass density gradient; convert the asphaltene weight percentage distribution to an OD distribution utilizing a predetermined correlation between asphaltene weight fraction and OD; and perform an optimization process to reduce differences between the OD distribution and the measured OD data to within a predetermined range and refine a biodegradation time of the predetermined diffusion model.

The upper and lower asphaltene weight fractions may be obtained based on the OD measured proximate the respective oil column ends. The upper and lower asphaltene weight fractions may be obtained utilizing the predetermined correlation between asphaltene weight fraction and OD. The predicted OD data may be based on a substantial lack of biodegradation within the oil column. The predetermined correlation between asphaltene weight fraction and OD may be a linear relationship determined empirically from data obtained from other wellbores, laboratory data, or other data obtained prior to conveying the downhole tool within the wellbore.

The instructions recorded on the non-transitory, computer-readable medium may further be for operating the downhole tool and surface equipment to: measure mass density of the fluid at the plurality of depths, wherein the upper and lower maltene partial densities are obtained based on the respective upper and lower asphaltene weight fractions and the mass density measured proximate the respective oil column ends; measure temperature of the fluid at the plurality of depths; determine that the oil column is a shallow formation having a maximum depth below the wellsite surface of about 1500 meters; determine that the oil column has experienced biodegradation based on the measured temperature data, the shallow formation determination, and a comparison of the measured OD data to predicted OD data; generate the predicted OD data based on a predetermined relationship between OD or asphaltene content and depth within the oil column assuming no biodegradation exists; estimate the mass density gradient with respect to depth within the oil column by fitting or interpolating the measured mass density data to a polynomial or other function; estimate the biodegradation time utilizing a fitting process and Fick's second law; and/or obtain a viscosity distribution along depth within the oil column based on the optimized OD distribution.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same purposes and/or achieving the same advantages of the embodiments introduced herein. A person having ordinary skill in the art should also realize that such equivalent constructions do not depart from the scope of the present disclosure, and that they may make various changes, substitutions and alterations herein without departing from the spirit and scope of the present disclosure.

What is claimed is:

1. A method, comprising:
   conveying a downhole tool within a wellbore, wherein the wellbore extends from a wellsite surface into a subterranean oil column, and wherein the downhole tool is in communication with surface equipment located at the wellsite surface; and
   operating at least one of the downhole tool and the surface equipment to:
      measure optical density (OD) of fluid at a plurality of depths within the oil column;
      obtain upper and lower asphaltene weight fractions of fluid proximate respective ends of the oil column based on the measured OD;
      obtain upper and lower maltene partial densities of the fluid proximate the respective oil column ends based on the respective upper and lower asphaltene weight fractions;
      obtain a maltene partial density distribution along depth within the oil column utilizing the upper and lower maltene partial densities and a predetermined diffusion model;
      obtain an asphaltene partial density distribution along depth within the oil column based on the maltene partial density distribution and a mass density gradient estimated with respect to depth within the oil column;
      obtain an asphaltene weight percentage distribution along depth within the oil column based on the asphaltene partial density distribution and the mass density gradient;
      convert the asphaltene weight percentage distribution to an OD distribution utilizing a predetermined correlation between asphaltene weight fraction and OD; and
      perform an optimization process to reduce differences between the OD distribution and the measured OD to within a predetermined range and refine a biodegradation time of the predetermined diffusion model.

2. The method of claim 1 further comprising operating at least one of the downhole tool and the surface equipment to obtain a viscosity distribution along depth within the oil column based on the optimized OD distribution.

3. The method of claim 1 wherein the upper and lower asphaltene weight fractions are obtained based on the OD measured proximate the respective oil column ends.

4. The method of claim 3 wherein the upper and lower asphaltene weight fractions are obtained utilizing the predetermined correlation between asphaltene weight fraction and OD.

5. The method of claim 1 further comprising operating at least one of the downhole tool and the surface equipment to measure mass density of the fluid at the plurality of depths, wherein the upper and lower maltene partial densities are obtained based on the respective upper and lower asphaltene weight fractions and the mass density measured proximate the respective oil column ends.

6. The method of claim 1 further comprising operating at least one of the downhole tool and the surface equipment to measure temperature of the fluid at the plurality of depths.

7. The method of claim 6 further comprising operating at least one of the downhole tool and the surface equipment to determine that the oil column is a shallow formation having a maximum depth below the wellsite surface of about 1500 meters.

8. The method of claim 7 further comprising operating at least one of the downhole tool and the surface equipment to determine that the oil column has experienced biodegradation based on the measured temperature data, the shallow formation determination, and a comparison of the measured OD to a predicted OD.

9. The method of claim 8 wherein the predicted OD is based on a substantial lack of biodegradation within the oil column.

10. The method of claim 8 further comprising operating at least one of the downhole tool and the surface equipment to generate the predicted OD based on a predetermined relationship between OD and depth within the oil column assuming substantially no biodegradation exists.

11. The method of claim 8 further comprising operating at least one of the downhole tool and the surface equipment to generate the predicted OD based on a predetermined relationship between asphaltene content and depth within the oil column assuming substantially no biodegradation exists.

12. The method of claim 1 further comprising operating at least one of the downhole tool and the surface equipment to estimate the mass density gradient with respect to depth within the oil column by fitting or interpolating the measured mass density data to a polynomial or other function.

13. The method of claim 1 wherein the predetermined correlation between asphaltene weight fraction and OD is a linear relationship determined empirically from data obtained from other wellbores, laboratory data, or other data obtained prior to conveying the downhole tool within the wellbore.

14. The method of claim 1 further comprising operating at least one of the downhole tool and the surface equipment to estimate the biodegradation time utilizing a fitting process and Fick's second law.

15. A system, comprising:
a downhole tool conveyable within a wellbore, wherein the wellbore extends from a wellsite surface into a subterranean oil column; and
surface equipment located at the wellsite surface and in communication with the downhole tool;
wherein the downhole tool and the surface equipment are collectively operable to:
measure optical density (OD) of fluid at a plurality of depths within the oil column;
obtain upper and lower asphaltene weight fractions of fluid proximate respective ends of the oil column based on the measured OD;
obtain upper and lower maltene partial densities of the fluid proximate the respective oil column ends based on the respective upper and lower asphaltene weight fractions;
obtain a maltene partial density distribution along depth within the oil column utilizing the upper and lower maltene partial densities and a predetermined diffusion model;
obtain an asphaltene partial density distribution along depth within the oil column based on the maltene partial density distribution and a mass density gradient estimated with respect to depth within the oil column;
obtain an asphaltene weight percentage distribution along depth within the oil column based on the asphaltene partial density distribution and the mass density gradient;
convert the asphaltene weight percentage distribution to an OD distribution utilizing a predetermined correlation between asphaltene weight fraction and OD; and
perform an optimization process to reduce differences between the OD distribution and the measured OD to within a predetermined range and refine a biodegradation time of the predetermined diffusion model.

16. The system of claim 15 wherein:
the upper and lower asphaltene weight fractions are obtained based on the OD measured proximate the respective oil column ends;
the upper and lower asphaltene weight fractions are obtained utilizing the predetermined correlation between asphaltene weight fraction and OD; and
the predetermined correlation between asphaltene weight fraction and OD is a linear relationship determined empirically from data obtained from other wellbores, laboratory data, or other data obtained prior to conveying the downhole tool within the wellbore.

17. The system of claim 15 wherein the downhole tool and the surface equipment are collectively further operable to:
measure mass density of the fluid at the plurality of depths, wherein the upper and lower maltene partial densities are obtained based on the respective upper and lower asphaltene weight fractions and the mass density measured proximate the respective oil column ends;
measure temperature of the fluid at the plurality of depths;
determine that the oil column is a shallow formation having a maximum depth below the wellsite surface of about 1500 meters;
determine that the oil column has experienced biodegradation based on the measured temperature data, the shallow formation determination, and a comparison of the measured OD to a predicted OD which is based on a substantial lack of biodegradation within the oil column;
generate the predicted OD data based on a predetermined relationship between OD or asphaltene content and depth within the oil column assuming no biodegradation exists;
estimate the mass density gradient with respect to depth within the oil column by fitting or interpolating the measured mass density data to a polynomial or other function;
estimate the biodegradation time utilizing a fitting process and Fick's second law; and
obtain a viscosity distribution along depth within the oil column based on the optimized OD distribution.

18. A computer program product, comprising:
a non-transitory, computer-readable medium; and
instructions recorded on the non-transitory, computer-readable medium for operating a downhole tool positioned within a wellbore and surface equipment in communication with the downhole tool to:
measure optical density (OD) of fluid at a plurality of depths within the oil column;

obtain upper and lower asphaltene weight fractions of fluid proximate respective ends of the oil column based on the measured OD;

obtain upper and lower maltene partial densities of the fluid proximate the respective oil column ends based on the respective upper and lower asphaltene weight fractions;

obtain a maltene partial density distribution along depth within the oil column utilizing the upper and lower maltene partial densities and a predetermined diffusion model;

obtain an asphaltene partial density distribution along depth within the oil column based on the maltene partial density distribution and a mass density gradient estimated with respect to depth within the oil column;

obtain an asphaltene weight percentage distribution along depth within the oil column based on the asphaltene partial density distribution and the mass density gradient;

convert the asphaltene weight percentage distribution to an OD distribution utilizing a predetermined correlation between asphaltene weight fraction and OD; and perform an optimization process to reduce differences between the OD distribution and the measured OD to within a predetermined range and refine a biodegradation time of the predetermined diffusion model.

19. The computer program product of claim 18 wherein:

the upper and lower asphaltene weight fractions are obtained based on the OD measured proximate the respective oil column ends;

the upper and lower asphaltene weight fractions are obtained utilizing the predetermined correlation between asphaltene weight fraction and OD; and the predetermined correlation between asphaltene weight fraction and OD is a linear relationship determined empirically from data obtained from other wellbores, laboratory data, or other data obtained prior to conveying the downhole tool within the wellbore.

20. The computer program product of claim 18 wherein the instructions recorded on the non-transitory, computer-readable medium are further for operating the downhole tool and surface equipment to:

measure mass density of the fluid at the plurality of depths, wherein the upper and lower maltene partial densities are obtained based on the respective upper and lower asphaltene weight fractions and the mass density measured proximate the respective oil column ends;

measure temperature of the fluid at the plurality of depths;

determine that the oil column is a shallow formation having a maximum depth below the wellsite surface of about 1500 meters;

determine that the oil column has experienced biodegradation based on the measured temperature data, the shallow formation determination, and a comparison of the measured OD to a predicted OD which is based on a substantial lack of biodegradation within the oil column;

generate the predicted OD data based on a predetermined relationship between OD or asphaltene content and depth within the oil column assuming no biodegradation exists;

estimate the mass density gradient with respect to depth within the oil column by fitting or interpolating the measured mass density data to a polynomial or other function;

estimate the biodegradation time utilizing a fitting process and Fick's second law; and obtain a viscosity distribution along depth within the oil column based on the optimized OD distribution.

\* \* \* \* \*